US006469035B1

(12) United States Patent
Cefali

(10) Patent No.: US 6,469,035 B1
(45) Date of Patent: *Oct. 22, 2002

(54) METHODS OF PRETREATING HYPERLIPIDEMIC INDIVIDUALS WITH A FLUSH INHIBITING AGENT PRIOR TO THE START OF SINGLE DAILY DOSE NICOTINIC ACID THERAPY TO REDUCE FLUSHING PROVOKED BY NICOTINIC ACID

(76) Inventor: Eugenio A. Cefali, Two Oakwood Blvd., Suite 140, Hollywood, FL (US) 33020

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 227 days.

(21) Appl. No.: 08/903,755

(22) Filed: Jul. 31, 1997

(51) Int. Cl.$^7$ ................................................ A61K 31/44
(52) U.S. Cl. ......................... 514/356; 514/27; 424/78.1
(58) Field of Search ................... 514/356, 27; 424/78.1

(56) References Cited

U.S. PATENT DOCUMENTS

| | | | | | |
|---|---|---|---|---|---|
| 3,674,836 A | * | 7/1972 | Creger | ........................ | 260/473 |
| 4,027,009 A | * | 5/1977 | Grier et al. | .................... | 424/78 |
| 4,911,917 A | * | 3/1990 | Kuhrts | ......................... | 424/10 |
| 4,965,252 A | * | 10/1990 | Kuhrts | ......................... | 524/54 |
| 5,126,145 A | * | 6/1992 | Evenstad et al. | ........... | 424/465 |
| 5,268,181 A | * | 12/1993 | O'Neill et al. | .............. | 424/465 |

FOREIGN PATENT DOCUMENTS

| | | | | |
|---|---|---|---|---|
| WO | 96/32942 | * | 10/1996 | ................. 424/465 |

* cited by examiner

Primary Examiner—James H. Reamer

(57) ABSTRACT

The present invention relates to pretreating individuals with an effective amount of a flush inhibiting agent for a sufficient period of time prior to the start of single daily dose nicotinic acid therapy to reduce the capacity of nicotinic acid to induce flushing reactions in such individuals during nicotinic acid therapy. In accordance with the present invention, the flush inhibiting agents are administered orally one to four times a day, and preferably one to two times per day, for between about 7 to about 14 days prior to the start of the nicotinic acid therapy. Examples of flush inhibiting agents include nonsteroidal anti-inflammatory agents. Aspirin is a preferred flush inhibiting agent and may be orally administered in daily doses of between about 80 mg to about 1000 mg, and preferably between about 80 mg and about 650 mg, and more preferably between about 80 mg and about 325 mg, during the pretreatment period. Also consistent with the present invention, the pretreatment therapy may be continued during and administered concurrently with the nicotinic acid therapy, in which the nicotinic acid is preferably administered once per day as a single dose during the evening hours or before or at bedtime. The nicotinic acid may be administered alone or in combination with HMG-CoA reductase inhibitors as well as other lipid-altering agents, like cholestyramine and colestipol.

30 Claims, No Drawings

METHODS OF PRETREATING HYPERLIPIDEMIC INDIVIDUALS WITH A FLUSH INHIBITING AGENT PRIOR TO THE START OF SINGLE DAILY DOSE NICOTINIC ACID THERAPY TO REDUCE FLUSHING PROVOKED BY NICOTINIC ACID

FIELD OF THE INVENTION

The present invention relates to pretreating individuals with an effective amount of a flush inhibiting agent for a sufficient period of time prior to the start of single daily dose nicotinic acid therapy to reduce the capacity of nicotinic acid to induce flushing reactions during such nicotinic acid therapy, and administering to the pretreated individuals nicotinic acid once per day as a single dose during the evening hours or before or at bedtime.

BACKGROUND

Hyperlipidemia or an elevation in serum lipids is associated with an increase incidence of cardiovascular disease and atherosclerosis. Specific forms of hyperlipidemia include, for example, hypercholesteremia, familial dysbetalipoproteinemia, diabetic dyslipidemia, nephrotic dyslipidemia and familial combined hyperlipidemia. Hypercholesteremia is characterized by an elevation in serum low density lipoprotein-cholesterol and serum total cholesterol. Low density lipoprotein (LDL-cholesterol) transports cholesterol in the blood. Familial dysbetalipoproteinemia, also known as Type III hyperlipidemia, is characterized by an accumulation of very low density lipoprotein-cholesterol (VLDL-cholesterol) particles called beta-VLDLs in the serum. Also associated with this condition, there is a replacement of normal apolipoprotein E3 with abnormal isoform apolipoprotein E2. Diabetic dyslipidemia is characterized by multiple lipoprotein abnormalities, such as an overproduction of VLDL-cholesterol, abnormal VLDL triglyceride lipolysis, reduced LDL-cholesterol receptor activity and, on occasion, Type III hyperlipidemia. Nephrotic dyslipidemia is difficult to treat and frequently includes hypercholesteremia and hypertriglyceridemia. Familial combined hyperlipidemia is characterized by multiple phenotypes of hyperlipidemia, i.e., Type IIa, IIb, IV, V or hyperapobetalipoproteinemia.

It is well known that the likelihood of cardiovascular disease can be decreased, if the serum lipids, and in particular LDL-cholesterol, can be reduced. It is also well known that the progression of atherosclerosis can be retarded or the regression of atherosclerosis can be induced if serum lipids can be lowered. In such cases, individuals diagnosed with hyperlipidemia or hypercholesteremia should consider lipid-lowering therapy to retard the progression or induce the regression of atherosclerosis for purposes of reducing their risk of cardiovascular disease, and in particular coronary artery disease.

Hypertriglyceridemia is also an independent risk factor for cardiovascular disease, such as coronary artery disease. Many people with hyperlipidemia or hypercholesteremia also have elevated triglyceride levels. It is known that a reduction in elevated triglycerides can result in the secondary lowering of cholesterol. These individuals should also consider lipid-lowering therapy to reduce their elevated triglycerides for purposes of decreasing their incidence of atherosclerosis and coronary artery disease.

Cholesterol is transported in the blood by lipoprotein complexes, such as VLDL-cholesterol, LDL-cholesterol, and high density lipoprotein-cholesterol (HDL-cholesterol). LDL carries cholesterol in the blood to the subendothelial spaces of blood vessel walls. It is believed that peroxidation of LDL-cholesterol within the subendothelial space of blood vessel walls leads to atherosclerosis plaque formation. HDL-cholesterol, on the other hand, is believed to counter plaque formation and delay or prevent the onset of cardiovascular disease and atherosclerotic symptoms. Several subtypes of HDL-cholesterol, such as $HDL_1$-cholesterol, $HDL_2$-cholesterol and $HDL_3$-cholesterol, have been identified to date.

In the past, there have been numerous methods proposed for reducing elevated cholesterol levels and for increasing HDL-cholesterol levels. Typically, these methods include diet and/or daily administration of lipid-altering or hypolipidemic agents. Another method proposed concerns periodic plasma dilapidation by a continuous flow filtration system, as described in U.S. Pat. No. 4,895,558.

Several types of hypolipidemic agents have been developed to treat hyperlipidemia or hypercholesteremia or normolipidemics diagnosed with cardiovascular disease. In general, these agents act (1) by reducing the production of the serum lipoproteins or lipids, or (2) by enhancing their removal from the serum or plasma. Drugs that lower the concentration of serum lipoproteins or lipids include inhibitors of HMG-CoA reductase, the rate controlling enzyme in the biosynthetic pathway of cholesterol. Examples of HMG-CoA reductase inhibitors include mevastatin, U.S. Pat. No. 3,983,140, lovastatin also referred to as mevinolin, U.S. Pat. No. 4,231,938, pravastatin, U.S. Pat. Nos. 4,346,227 and 4,410,629, lactones of pravastatin, U.S. Pat. No. 4,448,979, velostatin, also referred to as synvinolin, simvastatin, U.S. Pat. Nos. 4,448,784 and 4,450,171, rivastatin, fluvastatin, atorvastatin and cerivastatin. For other examples of HMG-CoA reductase inhibitors, see U.S. Pat. Nos. 5,217,992; 5,196,440; 5,189,180; 5,166,364; 5,157,134; 5,110,940; 5,106,992; 5,099,035; 5,081,136; 5,049,696; 5,049,577; 5,025,017; 5,011,947; 5,010,105; 4,970,221; 4,940,800; 4,866,058; 4,686,237; 4,647,576; European Application Nos. 0142146A2 and 0221025A1; and PCT Application Nos. WO 86/03488 and WO 86/07054.

Other drugs which lower serum cholesterol include, for example, nicotinic acid, bile acid sequestrants, e.g., cholestyramine, colestipol DEAESephadex (Secholex® and Polidexide®), probucol and related compounds as disclosed in U.S. Pat. No. 3,674,836, lipostabil (Rhone-Poulanc), Eisai E5050 (an N-substituted ethanolamine derivative), imantil (HOE-402) tetrahydrolipstatin (THL), isitigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanimid CL-277,082 and CL-283,546 (disubstituted urea derivatives), ronitol (which has an alcohol which corresponds to nicotinic acid), neomycin, p-aminosalicylic acid, aspirin, quarternary amine poly(diallyldimethylammonium chloride) and ionenes such as disclosed in U.S. Pat. No.

4,027,009, poly(diallylmethylamine) derivatives such as disclosed in U.S. Pat. No. 4,759,923, omega-3-fatty acids found in various fish oil supplements, fibric acid derivatives, e.g., gemfibrozil, clofibrate, bezafibrate, fenofibrate, ciprofibrate and clinofibrate, and other known serum cholesterol lowering agents such as those described in U.S. Pat. No. 5,200,424; European Patent Application No. 0065835A1, European Patent No. 164-698-A, G.B. Patent No. 1,586,152 and G.B. Patent Application No. 2162-179-A.

Nicotinic acid, also known as niacin, has been used for many years in the treatment of hyperlipidemia or hypercholesteremia. This compound has long been known to exhibit the beneficial effects of reducing total cholesterol, VLDL-cholesterol and VLDL-cholesterol remnants, LDL-cholesterol, triglycerides and apolipoprotein a, known as "Lp(a)," in the human body, while increasing desirable HDL-cholesterol.

Nicotinic acid has normally been administered three times per day after meals. This dosing regimen is known to provide a very beneficial effect on blood lipids as discussed in Knopp et al.; "Contrasting Effects of Unmodified and Time-Release Forms of Niacin on Lipoproteins in Hyperlipidemic Subjects: Clues to Mechanism of Action of Niacin"; *Metabolism* (34)7:642–647 (1985). The chief advantage of this profile is the ability of nicotinic acid to decrease total cholesterol, LDL-cholesterol, triglycerides and Lp(a) while increasing HDL-cholesterol particles. While such a regimen does produce beneficial effects, cutaneous flushing and the like still often occurs in the hyperlipidemics to whom the nicotinic acid is administered.

In order to avoid or reduce the cutaneous flushing resulting from nicotinic acid therapy, a number of agents have been suggested for administration with an effective antihyperlipidemic amount of nicotinic acid, such as guar gum as reported in U.S. Pat. No. 4,965,252, mineral salts as disclosed in U.S. Pat. No. 5,023,245, inorganic magnesium salts as reported in U.S. Pat. No. 4,911,917, and non-steroidal anti-inflammatories, such as aspirin, as disclosed in PCT Application No. 96/32942. These agents have been reported to avoid or reduce the cutaneous flushing side effect commonly associated with nicotinic acid dividend dose treatment.

Another method of avoiding or reducing the side effects associated with immediate release niacin is the use of extended or sustained release formulations. Extended or sustained release formulations are designed to slowly release the active ingredient from the tablet or capsule, which allows a reduction in dosing frequency as compared to the typical dosing frequency associated with conventional or immediate dosage forms. The slow drug release reduces and prolongs blood levels of the drug and, thus, minimizes or lessens the cutaneous flushing side effects that are associated with conventional or immediate release niacin products. Extended or sustained release formulations of niacin have been developed, such as Nicobid® capsules (Rhone-Poulenc Rorer), Endur-acin® (Innovite Corporation), and the formulations described in U.S. Pat. Nos. 5,126,145 and 5,268,181, which describe a sustained release niacin formulation containing two different types of hydroxy propyl methylcelluloses and a hydrophobic component.

Studies in hyperlipidemic patients have been conducted with a number of extended or sustained release niacin products. These studies have demonstrated that the extended or sustained release products do not have the same advantageous lipid-altering effects as immediate release niacin, and in fact have a worse side effect profile compared to the immediate release product. The major disadvantage of the sustained release formulations, as reported in Knopp et al.: *Metabolism,* 34(7):642–647 (1985), is the significantly lower reduction in triglycerides (−2% for the sustained release versus −38% for the immediate release) and lower increase in HDL-cholesterol (+8% for the sustained release versus +22% for the immediate release) and HDL2-cholesterol particles, which are known by the art to be most beneficial (−5% for the sustained release versus +37% for the immediate release).

Additionally, extended or sustained release niacin formulations are known to cause greater incidences of liver toxicity, as described in Henken et al.: *Am J Med,* 91:1991 (1991) and Dalton et al.: *Am J Med,* 93: 102 (1992). There is also great concern regarding the potential of these formulations in disrupting glucose metabolism and uric acid levels.

In a previous edition of the Journal of the American Medical Association (JAMA), an article appeared which presented research results investigating the liver toxicity problems associated with a sustained release form of nicotinic acid. "A Comparison of the Efficacy and Toxic Effects of Sustained-vs. Immediate-Release Niacin in Hypercholesterolemic Patients", McKenney et al., *JAMA,* 271( 9): 672 (Mar. 2, 1994). The article presented a study of twenty-three patients. Of that number, 18 or 78 percent were forced to withdraw because liver function tests (LFTs) increased indicating potential liver damage. The conclusion of the authors of that article was that the sustained release form of niacin "should be restricted from use."

A similar conclusion was reached in an article by representatives of the Food and Drug Administration and entitled "Hepatic Toxicity of Unmodified and Time-Release Preparations of Niacin", Rader et al.: *Am J Med,* 92:77 (January, 1992). Because of these studies and similar conclusions drawn by other health care professionals, the sustained release forms of niacin have experienced limited utilization.

HMG-CoA reductase inhibitors have also been used for many years to treat hyperlipidemia. These compounds are known to exhibit beneficial effects of reducing total cholesterol and LDL-cholesterol in the human body, and elevating HDL-cholesterol levels in some individuals. Grundy SM: *N Engl J Med* 319(1):24–32, at 25–26 and 31 (Jul. 7, 1988). The conversion of HMG-CoA to mevalonate is an early step in the biosynthesis of cholesterol. Inhibition of HMG-CoA reductase, which interferes with the production of mevalonate, is the basis by which the HMG-CoA reductase inhibitors exert their total cholesterol-lowering and LDL-cholesterol-lowering effects. Grundy S M: *N Engl J Med,* 319(1):24–32, at 25 and 26 (Jul. 7, 1988).

HMG-CoA reductase inhibitors are not without drawback, however. HMG-CoA reductase inhibitors are known to induce hepatotoxicity, myopathy and rhabdomyolysis, as reported in, for example, Garnett W R: *Am J Cardiol,* 78(Suppl 6A):20–25 (Sep. 26, 1996); The Lovastatin Pravastatin Study Group: *Am J Cardiol,* 71:810–815 (Apr. 1, 1993); Dujovne C A et al.: *Am J Med,* 91(Suppl 1B):25S–30S (Jul. 31, 1991); and Mantell G M et al.: *Am J Cardiol,* 66:11B–15B (Set. 18, 1990).

Moreover, on Page 1700, in column 3, of the Physicians' Desk Reference (PDR) 50th Ed., 1996, it reports that lovastatin, an HMG-CoA reductase inhibitor should be used with caution in patients who have a past history of liver disease, and that lovastatin therapy is contraindicated for those individuals with active liver disease or unexplained persistent elevations of serum transaminases. The 1996 PDR further reports on Page 1701, in column 1, that rhabdomyolysis has been associated with lovastatin therapy alone and when combined with lipid-lowering doses ($\geq 1$ g/day) of nicotinic acid, and that physicians contemplating combined therapy with lovastatin and lipid-lowering doses of nicotinic acid should carefully weigh the potential benefits and risks and should carefully monitor individuals for any signs and symptoms of muscle pain, tenderness, or weakness, particularly during the initial months of therapy and during any periods of upward dosage titration of either drug. The 1996 PDR further reports on page 1701, in column 1, that cases of myopathy have been associated with patients taking lovastatin concomitantly with lipid-lowering doses of nicotinic acid. The 1996 PDR also reports similar contraindications (1) for fluvastatin on page 2267, column 3, and on page 2268, column 1, (2) for pravastatin on page 767, column 1, and (3) for simvastatin on page 1777, column 2. Still further, the PDR recommends on page 768, column 3, that concomitant therapy with HMG-CoA reductase inhibitors and these agents [lipid lowering doses of nicotinic acid] is generally not recommended.

Notwithstanding the recommendations in the 1996 PDR, Grundy S M: *N Engl J Med,* 319(1):24–33 (Jul. 7, 1988), reports that HMG-CoA reductase inhibitors when used alone (at pages 29–30) and nicotinic acid when used alone (at page 24) are effective in reducing elevated cholesterol plasma levels. Grundy further reports on page 24, in column 2 at lines 10–25, that "[b]ecause of their efficacy . . . bile acid sequestrants (cholestyramine and colestipol) and niacin are probably the drugs of first choice for hypercholesteremia . . . Although these drugs can be highly effective and are satisfactory for use in many patients with high cholesterol levels, they unfortunately are not well tolerated by all patients. Therefore, in spite of their proved usefulness, bile acid sequestrants and niacin are not ideal cholesterol-lowering agents." Still further, Grundy reports on page 30, in column 1 at lines 13–17, that the " . . . administration of [HMG-CoA] reductase inhibitors twice a day is somewhat more effective than administration once a day, at the same total dosage." Grundy also reports on page 29, in column 1 at lines 7–11, " . . . that the combination of lovastatin and cyclosporine, gemfibrozil or nicotinic acid may predispose patients to myopathy and occasionally even to rhabdomyolysis." Still further, Grundy reports on page 30, in column 1 at lines 54–59, that "[the combination of lovastatin and niacin has not been shown to be safe in a controlled clinical trial; furthermore, a manifestation of an adverse interaction between the agents, such as myopathy, could occur." But see Gardner S F et al.: *Pharmacotherapy,* 16(3):421–423 (1996); Pasternak R C et al.: *Ann Intern Med,* 125(7):529–540 (Oct. 1, 1996); O'Keefe J H et al.: *Am J Cardiol,* 76:480–484 (Sep. 1, 1995); and Davignon J et al.: *Am J Cardiol,* 73:339–345 (Feb. 15, 1994).

In Vacek J L et al.: *Am J Cardiol,* 76:182–184 (Jul., 15, 1995), they report on page 183 that " . . . because of the present state of knowledge of the risks of hepatotoxicity with slow-release forms of nicotinic acid, this form of the drug should probably not be used [in combination with lovastatin] in future trials or clinical practice."

Consistent with the reports by Vacek J L et al. and the 1996 PDR, the article by Jacobson T A and Amorosa L F: *Am J Cardiol,* 73:25D–29D (May 26, 1994), reports, on pages 28D–29D, that because "[a]bnormalities in liver enzyme profiles and fulminant hepatic failure have also been associated with the use of niacin, particularly sustained-release preparations . . . the use of fluvastatin in combination with a sustained release niacin preparation cannot generally be recommended based upon this study, which only examined crystalline or immediate release niacin."

Therefore, it can be seen from the scientific literature that there is a need for development of lipid-altering or hypolipidemic pharmaceuticals and methods of delivering said pharmaceuticals which would provide patients with "balanced lipid alteration," i.e., reductions in total cholesterol, LDL-cholesterol, triglycerides and Lp(a), as well as increases in HDL particles, with an acceptable safety profile, especially as to liver toxicity, effects on glucose metabolism, uric acid levels, myopathy and rhabdomyolysis.

SUMMARY OF THE INVENTION

In brief, the present invention alleviates and overcomes certain of the above-identified problems and shortcomings of the present state of HMG-CoA reductase inhibitor therapy and nicotinic acid therapy through the discovery of novel HMG-CoA reductase/nicotinic acid pharmaceutical combinations for oral administration and methods of treatment with such pharmaceutical combinations.

In accordance with the present invention, a pharmaceutical combination for oral administration is provided to alter serum lipid levels in individuals, e.g., reducing hyperlipidemia and inhibiting atherosclerosis, without causing drug-induced hepatotoxicity, rhabdomyolysis, or myopathy. Generally speaking, the pharmaceutical combinations of the present invention comprise nicotinic acid, a derivative of nicotinic acid, a compound which is metabolized by the body to form nicotinic acid or any mixtures thereof in an extended release form, and an HMG-CoA reductase inhibitor. The pharmaceutical combinations are administered in amounts which are effective to alter or reduce serum lipids levels such as total cholesterol, VLDL-cholesterol, LDL-cholesterol, Lp(a) and triglycerides levels, and to enhance or increase HDL-cholesterol levels. This is accomplished without causing drug-induced hepatotoxicity, rhabdomyolysis or myopathy or adversely effecting glucose metabolism or uric acid levels, or at least without causing such side effects in at least an appreciable number of individuals to such a level that discontinuation of such therapy would be required.

In accordance with the present invention, the pharmaceutical combinations are administered once a day as a single oral dose. Preferably, and for those individuals on a typical day time schedule, the single oral dose is administered during evening hours, such as with or after their evening meals or at their bedtimes, to achieve in those individuals during the night effective in vivo levels for reducing total cholesterol, VLDL-cholesterol, LDL-cholesterol, Lp(a) and triglycerides levels and for enhancing or increasing HDL-cholesterol levels, some of which lipid components are biosynthesized predominantly at night in such individuals. For those individuals with typical night time, as opposed to day time, schedules, e.g., those individuals who work through the night and sleep during the day, it may be preferable to administer the pharmaceutical combinations of the present invention as a single oral dose at or near their day time bedtimes.

It also has been found that, when a pharmaceutical combination of the present invention is administered once a day as a single oral dose, the single dose provides additional total cholesterol, LDL-cholesterol, and triglyceride reduction effects over that which is obtained using the nicotinic acid alone. In fact, it has been found that the pharmaceutical combinations of the present invention, when administered as a single oral dose, reduces total cholesterol, LDL-cholesterol and triglycerides levels to a substantially greater extent than when either lipid-lowering drug is administered alone as a single oral dose in an equal dosage amount. Moreover, it has been found that the pharmaceutical combinations of the present invention, when administered as a single oral dose, increases HDL-cholesterol levels to a substantially greater extent than when the HMG-COA reductase inhibitor is administered alone as a single oral dose in an equal dosage amount. It is also believed that, when the pharmaceutical combinations of the present invention are administered once a day as a single dose, the single oral dose (1) is at least as effective as the combination of an equal or higher daily dosage of nicotinic acid administered in divided oral doses and an equal daily oral dosage of HMG-CoA reductase inhibitor administered separate from the divided doses of nicotinic acid, and (2) it has less capacity to provoke hepatotoxicity than the divided dose therapy.

Quite surprisingly, the pharmaceutical combinations of the present invention can be used to effectively treat, for instance, hyperlipidemia (e.g., cholesterol-related cardiovascular disease) and atherosclerosis of multiple etiology, and normolipidemics diagnosed with or predisposed to cardiovascular disease, without causing drug-induced liver damage, rhabdomyolysis or myopathy, or adversely effecting glucose metabolism or uric acid levels.

While the pharmaceutical combinations of the present invention contemplate the combination of (a) an HMG-CoA reductase inhibitor, and (b) nicotinic acid, as well as derivatives of nicotinic acid, compounds which the body metabolizes to nicotinic acid and any combinations thereof in an extended release form, the preferred pharmaceutical combinations in accordance with the present invention are pharmaceutical combinations for oral administration which are comprised of an HMG-CoA reductase inhibitor in an immediate release form, and nicotinic acid in an extended release form. Preferred HMG-CoA reductase inhibitors include atorvastatin, cervastatin, fluvastatin, lovastatin, pravastatin and simvastatin.

In carrying out a method of the present invention, the pharmaceutical combinations of the present invention can be administered to humans and other animal species, such as bovines, canines, felines, porcines, equines, sheep, rabbits, mice, rats, rodents, monkeys, etc. and, as such, may be incorporated into conventional systemic dosage forms, such as tablets, capsules, caplets, granules, beads, etc. Other lipid-altering or hypolipidemic agents as well as agents known to reduce or prevent all cutaneous flushing may be included in the pharmaceutical combinations or administered concomitantly with the pharmaceutical combinations in appropriate regimens which complement the beneficial effects of the pharmaceutical combinations of the present invention, so long as such additives do not defeat the objectives of the present invention.

The present invention also contemplates pretreating subjects with a nonsteroidal anti-inflammatory drug (NSAID) prior to the start of nicotinic acid therapy to reduce or eliminate nicotinic acid induced flushing which limits patient compliance. Pretreatment with low dosages of an NSAID, such as aspirin, when used according to a predosing schedule, cumulatively suppresses prostaglandin $D_2$ ($PGD_2$) production, making administration of nicotinic acid more tolerable. In accordance with the present invention, predosing a subject with an NSAID involves administering a low dose NSAID, such as aspirin, one to four times a day for at least about 7 days, and preferably for at least about 14 days, prior to nicotinic acid administration.

The doses administered should be carefully adjusted according to age, weight and condition of the patient, as well as the route of administration, dosage form and regimen and the desired result.

Thus, for oral administration, a satisfactory result may be obtained employing an HMG-CoA reductase inhibitor in dosages as indicated in, for example, the 1996 Physician's Desk Reference or package inserts for those products, such as in an amount within the range of from about 0.05 mg to about 160 mg, and preferably from about 0.05 to 80 mg, and more preferably from about 0.2 mg to about 40 mg, in combination with nicotinic acid in dosages normally employed, as indicated in the 1996 Physician's Desk Reference, for nicotinic acid, such as in an amount within the range of from about 250 mg to about 3000 mg, and preferably from about 500 mg to about 2500 mg, and most preferably from about 1000 mg to about 2000 mg, with the HMG-CoA reductase inhibitor and nicotinic acid being employed together in the same oral dosage form or in separate oral dosage forms taken at the same or about the same time. The nicotinic acid, therefore, may be daily dosed in increments of, for example, 250 mg, 500 mg, 750 mg, 1000 mg, 1500 mg, 2000 mg, 2500 mg and 3000 mg. Thus, the oral dosage forms of the present invention may include nicotinic acid in dosage amounts of, for example, 250 mg, 375 mg, 500 mg, 750 mg and 1000 mg.

It should be understood to those versed in this art that the exact dosing for an HMG-CoA reductase inhibitor will depend upon the particular HMG-CoA reductase inhibitor selected. Therefore, and in accordance with the present invention, the oral dosage forms may include lovastain, atorvastatin or pravastatin in dosage amounts of, for example, between about 10 mg and about 80 mg or more, such as 10 mg, 20 mg, 40 mg or 80 mg, simvastatin in dosage amounts of, for example, between about 5 mg and about 80 mg or more, such as 5 mg, 10 mg, 20 mg, 40 mg or 80 mg, fluvastatin in dosage amounts of, for example, between about 20 mg and 80 mg or more, such as 20 mg, 40 mg or 80 mg, and cerivastatin in dosage amounts of, for example, between about 0.05 mg and about 0.3 mg or more, such as 0.5 mg, 0.1 mg, 0.2 mg and 0.3 mg, to achieve a desired daily dosage.

Thus, and in accordance with the present invention, an oral solid dosage form, such as tablets, may contain the HMG-CoA reductase inhibitor in an amount of from about 0.05 mg to about 40 mg, and preferably from about 0.1 mg to about 20 mg, and nicotinic acid in an amount of from about 250 mg to about 1000 mg, and preferably from 500 mg to about 1000 mg. Examples of oral solid dosage forms in accordance with the present invention include: nicotinic acid/atorvastatin, fluvastatin, lovastatin, pravastatin, or simvastatin tablets in dosage strengths of, for instance, 250 mg/5 mg, 500 mg/5 mg, 750 mg/5 mg, 1000 mg/5 mg, 250 mg/7.5 mg, 500 mg/7.5 mg, 750 mg/7.5 mg 1000 mg/7.5 mg, 250 mg/10 mg, 500 mg/10 mg, 750 mg/10 mg, 1000 mg/10 mg, 250 mg/20 mg, 500 mg/20 mg, 750 mg/20 mg, 1000 mg/20 mg tablets, 250 mg/40 mg, 500 mg/40 mg, 750 mg/40 mg, and 1000 mg/40 mg; and nicotinic acid/cerivastatin tablets in dosage strengths of, for instance, 250 mg/0.05 mg, 500 mg/0.05 mg, 750 mg/0.05 mg, 1000 mg/0.05 mg, 250 mg/0.1 mg, 500 mg/0.1 mg, 750 mg/0.1 mg, 1000 mg/0.1 mg, 250 mg/0.15 mg, 500 mg/0.15 mg, 750 mg/0.15 mg, 1000 mg/0.15 mg tablets, 250 mg/0.2 mg, 500 mg/0.2 mg, 750 mg/0.2 mg, 1000 mg/0.2 mg tablets, 250 mg/0.3 mg, 500 mg/0.3 mg, 750 mg/0.3 mg and 1000 mg/0.3 mg tablets.

It is therefore an object of the present invention to provide a pharmaceutical combination for oral administration comprising (a) an HMG-CoA reductase inhibitor, and (b) nicotinic acid, derivatives of nicotinic acid, compounds which are metabolized by the body to form nicotinic acid and combinations thereof in a sustained release form for altering serum lipids to treat subjects, e.g., subjects diagnosed with hyperlipidemia, atherosclerosis and lipidemia in normolipidemics.

It is another object of the present invention to provide an oral solid pharmaceutical combination having extended release characteristics for the nicotinic acid, a derivative of nicotinic acid, a compound metabolized to nicotinic acid by the body or mixtures thereof, and having extended or immediate release characteristics for the HMG-CoA reductase inhibitor.

It is yet another object of the present invention to provide a method for employing a composition as above, for treating hyperlipidemics or normolipidemics diagnosed with or predisposed to cardiovascular disease, which results in little or no liver damage, myopathy or rhabdomyolysis.

At least one or more of the foregoing objects, together with the advantages thereof over the known art relating to the treatment of hyperlipidemia, which shall become apparent from the specification which follows, are accomplished by the invention as hereinafter described and claimed.

In general, the present invention provides an improved lipid-altering or antihyperlipidemia pharmaceutical combination of the oral type employing an effective lipid-altering or antihyperlipidemic amount of an HMG-CoA reductase inhibitor and nicotinic acid, wherein the pharmaceutical combination comprises compounding the nicotinic acid with, for example, from about 5% to about 50% parts by weight of hydroxy propyl methyl cellulose per hundred parts by weight of the tablet or formulation and coating the tablet with an HMG-CoA reductase inhibitor from about 0.01% to about 30% parts by weight of the tablet or formula.

The present invention also provides an orally administered lipid altering or antihyperlipidemia composition which comprises from about 0.01% to about 30% parts by weight of an HMG-CoA reductase inhibitor; from about 30% to about 90% parts by weight of nicotinic acid; and, from about 5% to about 50% parts by weight of hydroxy propyl methyl cellulose.

The present invention also includes a method of altering lipid levels in subjects, such as treating hyperlipidemia in a hyperlipidemic or lipidemia in a normolipidemic diagnosed with or predisposed to cardiovascular disease. The method comprises the steps of forming a composition which comprises effective lipid-altering amounts of an HMG-CoA reductase inhibitor and nicotinic acid, and an amount of excipients to provide immediate or extended release of the HMG-CoA reductase inhibitor and extended release of the nicotinic acid. The method also includes the step of orally administering the composition to the hyperlipidemic or normolipidemic nocturnally.

A method of treating hyperlipidemia in a hyperlipidemic or lipidemia in a normolipidemic according to the present invention, comprises dosing the hyperlipidemic or normolipidemic with an effective lipid-altering amount of an HMG-CoA reductase inhibitor and nicotinic acid, a derivative of nicotinic acid, a compound metabolized to nicotinic acid by the body or mixtures thereof. The dose is given once per day, preferably in the evening or at night, combined with a pharmaceutically acceptable carrier to produce a significant reduction in total cholesterol and LDL-cholesterol as well as a significant reduction in triglycerides and Lp(a), with a significant increase in HDL cholesterol.

The above features and advantages of the present invention will be better understood with the reference to the following detailed description and examples. It should also be understood that the particular methods and formulations illustrating the present invention are exemplary only and not to be regarded as limitations of the present invention.

DETAILED DESCRIPTION

By way of illustrating and providing a more complete appreciation of the present invention and many of the attendant advantages thereof, the following detailed description and examples are given concerning the novel methods and pharmaceuticals.

The present invention employs an HMG-CoA reductase inhibitor and nicotinic acid, a derivative of nicotinic acid or a compound other than nicotinic acid itself which the body metabolizes into nicotinic acid and mixtures thereof, thus producing the same effect as described herein. The nicotinic acid derivatives and other compounds specifically include, but are not limited to the following: nicotinyl alcohol tartrate, d-glucitol hexanicotinate, aluminum nicotinate, niceritrol, d,1-alpha-tocopheryl nicotinate, 6-OH-nicotinic acid, nicotinaria acid, nicotinamide, nicotinamide-N-oxide, 6-OH-nicotinamide, NAD, N-methyl-2-pyrridine-8-carboxamide, N-methyl-nicotinamide, N-ribosyl-2-pyridone-5-carboxide, N-methyl4-pyridone-5-carboxamide, bradilian, sorbinicate, hexanicite, ronitol, and esters of nicotinic acid such as lower alcohol esters like methyl, ethyl, propyl or butyl esters. Each an any such derivative or compound will be collectively referred to hereinabove by "nicotinic acid compound."

The specific HMG-CoA reductase inhibitors include, but are not limited to, lovastatin and related compounds as disclosed in U.S. Pat. No. 4,231,938, pravastatin and related compounds as reported in U.S. Pat. Nos. 4,346,227 and 4,448,979, mevastatin and related compounds as disclosed in U.S. Pat. No. 3,983,140, velostatin and simvastatin and related compounds as discussed in U.S. Pat. Nos. 4,448,784 and 4,450,171, fluvastatin, atorvastatin, rivastatin and fluindostatin (Sandoz XU-62-320), with fluvastatin, lovastatin, pravastatin, atorvastatin, simvastatin and cerivastatin being preferred. Other HMG-CoA reductive inhibitors which may be employed herein include, but are not limited to, pyrazole analogs of mevalonolactone derivatives as disclosed in U.S. Pat. No. 4,613,610, indent analogs of mevalonolactone derivatives as disclosed in PCT application WO 86/03488, 6-[2-(substituted-pyrrol-1-yl)alkyl]pyran-2-ones and derivatives thereof as disclosed in U.S. Pat. No. 4,647,576, Searle's SC-45355 (a 3-substituted pentanedioic acid derivative) dichloracetate, imidazole analogs of mevalonolactone as disclosed in PCT application WO 86/07054, 3-carboxy-2-hydroxy-propane-phosphoric acid derivatives as disclosed in French Patent No. 2,596,393, 2,3-di-substituted pyrrole, furan and thiophene derivatives as disclosed in European Patent Application No. 0221025 A14, naphthyl analogs of mevalonolactone as disclosed in U.S. Pat. No. 4,686,237, octahydro-naphthelenes such as disclosed in U.S. Pat. No. 4,499,289, keto analogs of lovastatin as disclosed in European Patent Application No. 0142146 A2, as well as other known HMG-CoA reductase inhibitors, such as those disclosed in GB Patent Nos. 2,205,837 and 2,205,838; and in U.S. Pat. Nos. 5,217,992; 5,196,440; 5,189,180; 5,166,364; 5,157,134; 5,110,940; 5,106,992; 5,099,035; 5,081,136; 5,049,696; 5,049,577; 5,025,017; 5,011,947; 5,010,105; 4,970,221; 4,940,800; 4,866,058; 4,686,237.

As stated hereinabove, HMG-CoA reductase inhibitors and nicotinic acid have been employed in the past for the treatment of hyperlipidemia, which condition is characterized by the presence of excess fats such as cholesterol and triglycerides, in the blood stream. According to one aspect of the present invention, an extended or sustained release composition of nicotinic acid coated with an immediate release coating of an HMG-COA reductase inhibitor is prepared as an example. By "extended release" or "sustained release" it is understood to mean a composition which when orally administered to a patient to be treated, the active ingredient like an HMG-COA reductase inhibitor, nicotinic acid, a nicotinic acid compound or mixtures thereof will be released for absorption into the blood stream over a period of time. For example, it is preferred that in a dosage of about 1500 milligrams (hereinafter "mgs") of nicotinic acid, approximately 100 percent of the nicotinic acid will be released to the blood stream in about 4 to about 8 hours and preferably within about 6 hours following ingestion.

While the nicotinic acid is released from the pharmaceutical combination in a sustained release manner, the HMG-CoA reductase inhibitors can be formulated for immediate or extended release following ingestion. By "immediate release," it is understood to mean that the HMG-CoA reductase inhibitor, which when orally administered to a patient to be treated, will be completely released from the composition for absorption into the blood stream within about 30 minutes following ingestion.

A specific sustained release composition according to the present invention employs an effective lipid-altering amount of nicotinic acid coated with an effective lipid-altering amount of an HMG-COA reductase inhibitor. By "effective lipid-altering amount" or "effective antihyperlipidemic amount" it is understood to mean an amount which when orally administered to a patient to be treated, will have a beneficial effect upon the physiology of the patient, to include at least some lowering of; one or more of the following, total cholesterol, LDL-cholesterol, triglycerides and Lp(a) and at least some increase in HDL-cholesterol, and more particularly an increase in, e.g., $HDL_2$-cholesterol and/or $HDL_3$-cholesterol, in the patient's blood stream. The beneficial effect will also include some decreases in the total cholesterol to HDL-cholesterol ratio and in the LDL-cholesterol-HDL-cholesterol ratio in the patient's blood stream. In some individuals, the beneficial effect may also include reduction in apolipoprotein B, reduction in apolipoprotein E and/or an increase in apolipoprotein A-I. An exemplary effective lipid-altering amount of nicotinic acid would be from about 250 mg to about 3000 mg of nicotinic acid to be administered according to the present invention, as will be more filly describe hereinbelow. An exemplary effective lipid-altering amount of an HMG-CoA reductase inhibitor would be from about 0.1 mg to about 80 mg. These amounts will of course vary, dependent upon a number of variables, including the psychological needs of the patient to be treated.

Preferably, there is also included in a sustained release composition according to the present invention, a swelling or sustained release agent which is compounded with the nicotinic acid, and/or nicotinic acid compounds, such that when the composition is orally administered to the patient, the swelling agent will swell over time in the patient's gastrointestinal tract, and release the active nicotinic acid, and/or nicotinic acid compound over a period of time. As is known in the art, such swelling agents and amounts thereof, may be preselected in order to control the time release of the active nicotinic acid ingredient. Such swelling agents include, but are not limited to, polymers such as sodium carboxymethylcellulose and ethylcellulose and waxes such as bees wax and natural materials such as gums and gelatins or mixtures of any of the above. Because the amount of the swelling agent will vary depending upon the nature of the agent, the time release needs of the patient and the like, it is preferred to employ amounts of the agent which will accomplish the objects of the invention.

An exemplary and preferred swelling agent is hydroxy propyl methyl cellulose, in an amount ranging from about 5% to about 50% parts by weight per 100 parts by weight of tablet or formulation. A preferred example will ensure a sustained time release over a period of approximately 4–8 hours.

A binder may also be employed in the present compositions. While any known binding material is useful in the present invention, it is preferred to employ a material such as one or more of a group of polymers having the repeating unit of 1-ethenyl-2-pyrrolidinone. These polyvinyl pyrrolidinone polymers generally have molecular weights of between about 10,000 and 700,000, and are also known as "povidone or PVP."

Amounts of the binder material will of course, vary depending upon the nature of the binder and the amount of other ingredients of the composition. An exemplary amount of povidone in the present compositions would be from about 1% to about 5% by weight of povidone per 100 parts by weight of the total formulation.

Processing aids such as lubricants, including stearic acid, magnesium stearate, glyceryl behenate, talc and colloidal silicon dioxide, may also be employed, as is known in the art. An exemplary amount of a lubricant, such as stearic acid, in the present compositions would be from about 0.5% to about 2.0% by weight per 100 parts by weight of tablet or formulation.

Also in accordance with the present invention, the sustained release compositions containing the nicotinic acid and/or nicotinic acid compounds are preferably coated with an HMG-CoA reductase inhibitor for immediate release following oral administration. An exemplary coating in accordance with the present invention comprises an HMG-CoA reductase inhibitor, a plasticizer, film forming and/or coating agent and a coloring agent. Specific examples of plasticizers include, but are not limited to, benzyl benzoate, chlorobutanol, dibutyl sebacate, diethyl phthalate, glycerin, mineral oil and lanolin alcohols, petrolatum and lanolin alcohols, polyethylene glycol, propylene glycol, sorbitol, triacetin and triethyl citrate. An exemplary amount of a plasticizer utilized in the coatings of the present invention would be from about 0.01% to about 5% by weight of the tablet.

Specific examples of film forming and/or coating agents include, but are not limited to, carboxymethylcellulose sodium, carnauba wax, cellulose acetate phthalate, cetyl alcohol, confectioner's sugar, ethylcellulose, gelatin, hydroxyethyl cellulose, hydroxy propyl cellulose, hydroxy propyl methyl cellulose, liquid glucose, maltodextrin, methyl cellulose, microcrystalline wax, polymethacrylates, polyvinyl alcohol, shellac, sucrose, talc, titanium dioxide and zein. An exemplary amount of a film forming/coating agent in the present coatings would be from about 0.01% to about 5% by weight of the tablet. Generally speaking to prepare a coating in accordance with the present invention, an HMG-CoA reductase inhibitor is suspended or dissolved in an aqueous-solution of polyethylene glycol and hydroxy propyl methyl cellulose and then sprayed on the sustained release tablets by a film-coating process to a thickness containing an effective antihyperlipidemic amount of an HMG-CoA reductase inhibitor. Examples of suitable coating thicknesses in accordance with the present invention are from about 0.1 mm to about 2.0 mm or more.

Coated sustained release tablets of various sizes can be prepared, e.g., of about 265 mg to 1650 mg in total weight, containing both of the active substances in the ranges described above, with the remainder being a physiologically acceptable carrier of other materials according to accepted pharmaceutical practice. These coated tablets can, of course, be scored to provide for fractional doses. Gelatin capsules can be similarly formulated.

Consistent with the present invention, such dosage forms should be administered to individuals on a regimen of one dose per day, preferably during the evening hours.

In order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Combinations of an HMG-CoA reductase inhibitor and nicotinic acid and/or nicotinic acid compounds in the same pharmaceutical are more convenient and are therefore preferred, especially in the coated tablet or caplet form for oral administration. Alternatively, however, the pharmaceutical combinations of the present invention may comprise two distinct oral dosage forms which may be administered concomitantly, where one oral dosage form is formulated for extended or sustained release of nicotinic acid or a nicotinic acid compound or mixtures thereof, and the other oral dosage form is formulated for extended or immediate release of an HMG-CoA reductase inhibitor.

Optionally, the oral pharmaceutical combinations of the present invention may include other active ingredients. In addition, the present invention contemplates that other active ingredients may be administered concurrently with the pharmaceutical combinations of the present invention. Examples of other active ingredients include anti-lipidemic agents and flushinhibiting agents. Specific examples of anti-lipidemic agents include but are not limited to, bile acid sequestrants, e.g., cholestyramine, colestipol DEAESephadex (Secholex® and Polidexide®), probucol and related compounds as disclosed in U.S. Pat. No. 3,674,836, lipostabil (Rhone-Poulanc), Eisai E5050 (an N-substituted ethanolamine derivative), imanixil (HOE-402) tetrahydrolipstatin (THL), isitigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanimid CL-277,082 and CL-283,546 (disubstituted urea derivatives), neomycin, p-aminosalicylic acid, aspirin, quarternary amine poly (diallyldimethylammonium chloride) and ionenes such as disclosed in U.S. Pat. No. 4,027,009, poly (diallylmethylamine) derivatives such as disclosed in U.S. Pat. No. 4,759,923, omega-3-fatty acids found in various fish oil supplements, fibric acid derivatives, e.g., gemfibrozil, clofibrate, bezafibrate, fenofibrate, ciprofibrate and clinofibrate, and other known serum cholesterol lowering agents such as those described in U.S. Pat. No. 5,200,424; European Patent Application No. 0065835A1, European Patent No. 164-698-A, G.B. Patent No. 1,586,152 and G.B. Patent Application No. 2162-179-A.

Specific examples of flush-inhibiting agents include, but are not limited to, nonsteroidal anti-inflammatory drugs such as aspirin and salicylate salts; propionic acids such as ibuprofen, flurbiprofen, fenoprofen, ketoprofen, naproxen, sodium naproxen, carprofen and suprofen; indoleacetic acid derivatives such as indomethacin, etodolac and sulindac; benzeneacetic acids such as aclofenac, diclofenac and fenclofenac; pyrroleacetic acids such as zomepirac and tolmectin; pyrazoles such as phenylbutazone and oxyphenbutazone; oxicams such as piroxicam; and anthranilic acids such as meclofenamate and mefenamic acid.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Additional illustrations of adjuvants which may be incorporated in the tablets are the following: a binder such as gum tragacanth, acacia, corn starch, potato starch, alginic acid or the like; a sweetening agent such as sucrose, aspartase, lactose or saccharin; a flavoring such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both.

Some of the active agents described above form commonly known pharmaceutically acceptable salts, such as alkali metal and other common basic salts or acid addition salts, etc. References to the base agents are therefore intended to include those common salts known to be substantially equivalent to the parent compound.

In carrying out the objective of the present invention, the nicotinic acid, nicotinic acid compounds and/or HMG-CoA reductase inhibitors may be formulated into sustained release granules, sustained release particles, sustained release coated particles or sustained release beads or pellets according to any method known to the art for the manufacture of pharmaceutical compositions for incorporation into a variety of oral dosage forms suitable for oral use, such as tablets, such as rapidly disintegrating tablets, compression coated tablets, enteric coated tablets, capsules, caplets, sachets for sprinkle administration, and the like. In addition, the HMG-CoA inhibitors may be formulated into immediate release granules or immediate release coated raw materials for incorporation into the oral dosage forms of the present invention.

A preferred nicotinic acid sustained release dosage form is the Niaspan® tablets. The Niaspan® tablets can be modified consistent with the present invention to include an HMG-Co reductase inhibitor during the formation of the Niaspan® granules or during the manufacture of the Niaspan® tablet blend prior to compression into the Niaspan® tablets to formulate a pharmaceutical combination of the present invention in which the nicotinic acid and HMG-CoA reductase inhibitor are in a sustained release form. Alternatively, the Niaspan® tablets may be coated with a coating containing an HMG-CoA reductase inhibitor in immediate release form to formulate a pharmaceutical combination of the present invention in which the nicotinic acid is in an extended release form and the HMG-CoA reductase inhibitor is in an immediate release form.

The present invention also contemplates other combined dosage forms containing an HMG-CoA reductase inhibitor and nicotinic acid, a nicotinic acid compound or mixtures thereof For instance, such combined dosage forms include bilayer or multilayer tablets, capsules or sachets containing, for example, immediate or sustained release granules of an HMG-CoA reductase inhibitor and sustained release granules of nicotinic acid, a nicotinic acid compound or mixtures thereof. Bilayer or multilayer tablets may be manufactured utilizing techniques well known in this art, such as by lightly prestamping a nicotinic acid layer containing sustained release nicotinic acid granules, adding a layer containing an HMG-CoA reductase inhibitor either deficient in or containing a sustained release or swelling agent, and compressing the combined powder to form the bilayer tablet. Optionally, the HMG-CoA reductase layer may further contain other agents, such as a flush inhibiting agent, like as aspirin.

In a further embodiment, the pharmaceutical combination of the present invention may be enterically coated to delay disintegration and absorption in the gastrointestinal tract. For example, (1) sustained release nicotinic acid granules or immediate or sustained release HMG-CoA reductase inhibitor granules may be individually enterically coated and compressed to form a tablet or a layer of a bilayer tablet, or (2) the tablet itself or a layer thereof may be coated with an enteric coating.

Enterically coated dosage forms do not necessarily dissolve or become absorbed by humans until they pass through the low pH environment of the stomach and pass into the relatively higher pH of the small intestine. Typical materials conventionally used as enteric coatings include, but are not limited to, cellulose acetate phthalate, polyvinylacetate phthalate, hydroxypropyl methylcellulose phthalate and methacrylic acid-methyl methacrylate copolymers. Such materials can be used individually or in combination. Additional formulating agents, such as plasticizers (e.g., one or more polyethylene glycols or propylene glycol) may be added to ensure physical strength and processability, e.g., to prevent cracking due to stress, low humidity or other factors.

Enterically coated nicotinic acid or HMG-CoA reductase inhibitors granules can be prepared in a fluid bed granulator by coating or agglomerating niacin powder with one or more enteric coating materials, such that microspheres or small particles of enterically coated nicotinic acid are formed. Alternatively, a whole tablet or capsule comprising an HMG-CoA reductase inhibitor and/or nicotinic acid can be coated with enteric coating materials.

Typically, the enteric coating process comprises coating the dosage form with a plurality of layers, e.g., one or two layers or more, of enteric coating material, like a methacrylate polymer such as EUDRAGIT S-100, available from Rohm, preferably by dipping the weight tablet or capsule into a freshly prepared solution of the material for five seconds. The solution of enteric coating material(s) may be prepared by dissolving an appropriate amount of material in, e.g., 100 ml of a 4:6 mixture of acetone and isopropyl alcohol. After each immersion, the coating is allowed to dry in air, e.g., for 30 minutes, prior to the next five-second immersion. A single coating is usually adequate to prevent the capsule or table from dissolving in the stomach. Alternatively, the granules, tablets or capsules may be coated or spray-dried in standard coating machines such as those typically employed in the pharmaceutical industry.

The present invention also contemplates methods for pretreating subjects, prior to the start of nicotinic acid or nicotinic acid combination therapy, with a nonsteroidal anti-inflammatory drug (NSAID) in an amount effective to inhibit or reduce prostaglandin $PGD_2$ synthesis, so that any flush reaction induced by the nicotinic acid therapy is lessened or prevented. In carrying out this aspect of the present invention, the pretreatment should start at least about 7 days prior to administration of the nicotinic acid, and preferably for at least about 14 days. While pretreatment for a shorter duration may not provide a subject with adequate protection against flushing, some protective effect may be observed and, thus, such shorter pretreatment periods may be practiced within the scope of the present invention.

During pretreatment of subjects with an NSAID, the NSAID selected is orally administered in at least one to four or more doses daily. However, while three or fewer doses per day is preferred, one or two doses per day are preferential for the convenience and improved compliance of the subjects. The NSAID may be administered orally as an immediate or extended release dosage form. Of course, if an extended release dosage form is selected, the NSAID can be administered fewer times daily then a comparable immediate release dosage form, while providing similar protection against nicotinic acid-induced flushing.

While it is preferable to take an NSAID during pretreatment, the present invention also contemplates continued administration of the NSAID during the nicotinic acid or nicotinic acid compound treatment. This can be accomplished by taking the NSAID as a separate dosage form on a daily basis, or by taking a pharmaceutical component of the present invention which includes an NSAID.

Particularly preferred NSAIDs include indomethacin, ibuprofen, naproxen, aspirin, ketoprofen, flurbiprofen, phenylbutazone, and piroxicam. These NSAIDs may be administered in their usual doses for treatment of inflammation. Aspirin is especially preferred. Aspirin may be administered in daily dosages of at least between about 60 mg and about 1000 mg, and more preferably at least between about 80 mg and 650 mg, and most preferably between about 80 mg and 325 mg. Even though higher daily dosages of aspirin may be consumed to suppress flushing in accordance with the present invention, there is risk that these higher dosages, as well as the high end of the preferred dosages, could induce gastrointestinal upset and ulceration.

While extended release forms are commercially available for some NSAIDs, other extended release formulations may be prepared by conventional methods from those versed in the art, or by blending the NSAID with the nicotinic acid during granules or during the powder blending stage pursuant to the methods described herein to generate a pharmaceutical combination comprised of nicotinic acid and an NSAID in extended release form. Alternatively, the NSAID could be blended with an HMG-CoA reductase inhibitor in a coating for immediate release of the NSAID. As a further alternative contemplated by the present invention, extended release nicotinic acid tablets, such as Niaspan®, can be enterically coated for delayed release, which then may be coated with a coat comprised of an HMG-CoA reductase and an NSAID for immediate release.

In a further aspect of the present invention, the solid pharmaceutical combinations for oral administration may be formulated into various shapes. For example, tablets may be round/flat, round/convex, oval/flat, oval/convex, or capsule (caplet) in shape, whereas capsules may be round or elongated in shape. It is presently believed that when tablets are coated in accordance with the present invention, the coatings can be improved if the tablets are in an oval/convex shape. For instance, it is believed that by formulating the sustained release nicotinic acid tablets, such as Niaspan® tablets, into oval/convex shapes, the coatings containing an HMG-CoA reductase inhibitor are improved, as compared to similar coatings on tablets having, for example, a capsule (caplet) shape.

The formulations as described above will be administered for a prolonged period, that is, for as long as the potential for elevated serum cholesterol and atherosclerosis remains or the symptoms continue. A dosing period of at least about 4 weeks maybe required to achieve a desired therapeutic benefit.

The disclosures of the U.S. patents and patent applications mentioned and cited herein are incorporated herein by reference in their entireties.

Examples of various embodiments of the present invention will now be further illustrated with reference to the following examples.

EXAMPLE I

In order to demonstrate the effectiveness of the compositions and method of the present invention over known antihyperlipidemia compositions and methods heretofore known in the art, a number of substantially identical composition were prepared according to the disclosure hereinabove. The composition ingredients and amounts are listed in TABLE IA hereinbelow.

TABLE IA

Test Tablet Composition

| Ingredient | 375 mg | 500 mg | 750 mg |
| --- | --- | --- | --- |
| Nicotinic Acid | 375.0 | 500.0 | 750.0 |
| Hydroxy propyl methyl cellulose | 188.7 | 203.0 | 204.7 |
| Povidone | 12.9 | 17.2 | 25.9 |
| Stearic Acid | 5.8 | 7.3 | 9.9 |
| TOTAL | 582.4 mg | 727.5 mg | 990.5 mg |

The ingredients were compounded together to form a tablet. More specifically, Niaspan® once-daily tablets in accordance with the present invention utilize a hydrophilic matrix controlled drug delivery system. This is a dynamic system composed of polymer wetting, polymer hydration and polymer disintegration/dissolution. The mechanism by which drug release is controlled depends on, for example, initial polymer wetting, expansion of the gel layer, tablet erosion and niacin solubility. After initial wetting, the hydrophilic polymer starts to partially hydrate, forming a gel layer. As water permeates into the tablet increasing the thickness of the gel layer, drug diffuses out of the gel layer. As the outer layer of the tablet becomes fully hydrated it erodes. It is believed that this erosion results in additional drug release.

The controlled release from this matrix delivery system can be modified depending on the type and molecular weight of hydrophilic polymer used.

A Niaspan® formulation consists of Niacin, Methocel® E10M Premium, Povidone K90 and Hystrene 5016 (stearic acid). Methocel® E10M Premium is utilized as a controlled-release agent in the Niaspan® formulation. Methocel is a partly O-methylated and O-(2-hydroxypropylated) cellulose and is available in several grades which vary in terms of viscosity and degree of substitution. Methocel is manufactured by Dow Chemical.

Povidone K90 is employed as a granulating/binding agent in a Niaspan® formulation. Povidone is a synthetic polymer consisting of linear 1-vinyl-2-pyrrolidone groups, the degree of polymerization of which results in polymers of various molecular weights, or as indicated above. It is characterized by its viscosity in aqueous solution, relative to that of water, expressed as a K-value, ranging from 10–120. Povidone K90 has an approximate molecular weight of 1,000,000. Povidone is a hygroscopic, water soluble material. Povidone K90 present in a Niaspan® formulation is manufactured by ISP (International Speciality Products). Hystene 5016 is utilized as an external lubricant in the Niaspan® formulation. Hystrene 5016 is a mixture of stearic acid and palmitric acid. The content of stearic acid is not less than about 40.0% and the sum of the two acids is not less than about 90.0%. Hystrene 5016 is manufactured by Witco. Refer to Table IB for Niaspan® formulation details.

Qualitatively, the four tablet strength formulations are identical. The major component of each formulation is a granulated mixture of Niacin, Methocel E10M and Povidone K90. The granulation process improves compression properties.

TABLE IB

Niaspan ® Tablet Formulations

| Niaspan ® Product | 375 mg Tablets | 500 mg Tablets | 750 mg Tablets | 1000 mg Tablets |
|---|---|---|---|---|
| Formulation, % Tablet | | | | |
| Niacin | 64.4 | 70.5 | 77.4 | 83.1 |
| Methocel E10M Premium (Intragranular) | 7.4 | 8.1 | 8.9 | 9.5 |
| Povidone K90 | 2.2 | 2.4 | 2.7 | 2.9 |
| Methocel E10M Premium (Extragranular) | 25.0 | 18.0 | 10.0 | 3.5 |
| Hystrene 5016 (Stearic Acid) | 1.0 | 1.0 | 1.0 | 1.0 |
| Tablet weight, mg | 582.5 | 709.5 | 968.6 | 1203.6 |

Niaspan® formulations are presented in white caplet shape tablets. Caplet dimensions differ with respect to product strength. The 375 mg and 500 mg Niaspan® tablets are compressed with tooling measuring approximately 0.687" in length×0.281" by width. The length and width of the 750 mg and 1000 mg tooling measures approximately 0.750"×0.320". Target tablet weight and hardness dictate thickness across the four Niaspan® products. The production of the Niaspan® tablets will now be described generally as set forth below.

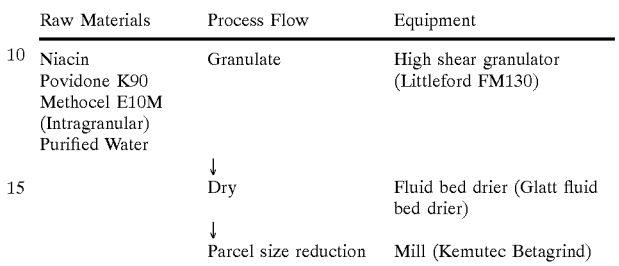

Niaspan® Granulation Process Description

Niaspan® granulation raw materials are dispensed and granulated in a high shear granulator. The wet granules are sieved into a fluid bed drier and are dried. When the drying process is complete, the granules are milled. Milling ensures uniform particle size distribution throughout the Niaspan® granulation.

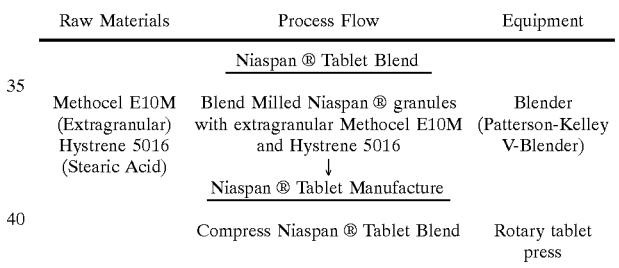

Niaspan® Tablet Process Description

A Niaspan® tablet blend is manufactured by blending the Niaspan® granulation, extragranular Methocel E10M and Hystrene 5016. The quantities of each Niaspan® tablet blend component will depend on the particular Niaspan® dose being manufactured (refer to Table IB). A Niaspan® tablet blend is compressed to form Niaspan® tablets. Niaspan® tablet physical properties will vary depending on the particular Niaspan® dose being manufactured.

Production of Niaspan® tablets will now be discussed in greater detail. The initial stage of manufacturing is the same for all four tablet strengths of Niaspan® (375, 500, 750, and 100 mg). One batch of Niaspan® granulation is comprised of four individual 40.0 kg units of granulation which are processed separately, but under like conditions. The four individual granulations are sampled and tested individually and subsequently released for blending. The base granulation is not strength specific and may be used to manufacture any tablet strength of Niaspan®.

The ingredients in the base granulation are set forth in Table IC below:

TABLE IC

| Component | Function | Quantity per kilogram granulation (kg) | % per kilogram granulation | Quantity per 160.00 kg batch (kg) |
|---|---|---|---|---|
| Niacin, USP | Drug Substance | 0.87 | 87.00 | 139.20 |
| Povidone, USP | Binder | 0.03 | 3.00 | 4.80 |
| Methocel USP, E10M Premium | Controlled-Release Agent | 0.10 | 10.00 | 16.00 |
| Purified Water, USP* | Granulation Reagent | 0.00* | 0.00* | 48.00 |
| Total | | | | 160.00 |

*Purified Water, USP is used as a granulation reagent and does not appear in the finished granulation.

Raw materials are quantitatively dispensed into appropriately labeled double polyethylene-lined containers using calibrated scales. Purified Water, USP is dispensed into an appropriate vessel from which it is later pumped during the wet-massing operation.

A Littleford FM130 granulator is charged with approximately one half of the Niacin, USP required for the process unit (~17.4 kg) followed by about 4.00 kg of Methocel, USP E10M Premium CR Grade; about 1.20 kg of Povidone, USP; and the balance of the Niacin, SP (~17.40 kg). The powder bed is dry mixed in the Littleford FM130 granulator, with choppers on, for approximately 1 minute. At the completion of the 1-minute pre-mix cycle, about 12.0±0.05 kg of Purified Water, USP are sprayed onto the powder bed at a rate of about 2.40±0.24 kg/miniute. Immediately following the addition of the Purified Water, USP, the unit is granulated for about 5 minutes.

The granulated unit is discharged into double polyethylene-lined containers and then manually loaded into a Glatt bowl while being passed through a #4 mesh screen. The Glatt bowl is loaded into a Glatt TFO-60 fluid-bed drier with an inlet air temperature setting of about 70° C.±5° C. The unit is dried until a moisture level of ≦1.0% is obtained as determined using a Computrace) Moisture Analyzer, model MA5A. The dried granulation is discharged inot appropriately labeled, double polyethylene-lined drums and reconciled.

The dried and reconciled granulation is passed through a Kemutec BetaGrind mill equipped with a 1.5 mm screen and running at approximately 1500 RPM. The milled granulation is collected into appropriately labeled, double polyethylene-lined drums and reconciled. The milled granulation is sampled and tested by Quality Control and released prior to further processing.

The released granulation units are charged to a Patterson-Kelley 20 ft$^3$ V-blender after which they are blended together for about 10±1 minutes and then discharged to appropriately labeled, double polyethylene-lined containers.

As stated above, Niaspan® tablets are formulated from a common granulation which is blended with appropriate quantities of Methocel, USP E10M Premium CR Grade and Stearic Acid, NF to achieve the final dosage formulation. Tables IA and IB describe the formulation for each Niaspan® tablet strength, 375 mg, 500 mg, 750 mg, and 1000 mg, respectively.

Two study groups consisting of eleven and fourteen patients each were formed. Blood samples were taken from the patients, and tested for total cholesterol, LDL cholesterol, triglycerides and HDL cholesterol to establish baseline levels from which fluctuations in these lipids could be compared. The patients were then placed upon a regimen of the above discussed tables, totaling approximately 1500 mg of nicotinic acid, once per day before going to bed. After eight weeks of this regimen, the patients were again tested for lipid profiles. The results of the tests conducted at eight weeks, showing the changes in the lipid profiles as a percentage change from the baseline, are reported in the table hereinbelow. Positive numbers reflect percentage increases and negative numbers reflect percentage decreases in this table.

TABLE II

Patient Study Lipid Profile Data

| Pt. No | Total-C | LDL-C | Apo B | Trigs | HDL-C | HDL$_2$C | Lp(a) |
|---|---|---|---|---|---|---|---|
| Group A | | | | | | | |
| 1 | −8.2 | −12.0 | NA | −17.3 | 22.0 | NA | NA |
| 2 | −5.9 | −27.0 | NA | −28.7 | 65.0 | NA | NA |
| 3 | −15.1 | −13.0 | NA | −22.0 | −9.1 | NA | NA |
| 4 | −3.3 | −10.0 | NA | 61.6 | 3.8 | NA | NA |
| 5 | −16.5 | −17.7 | NA | −28.8 | 11.1 | NA | NA |
| 6 | −12.4 | −25.9 | NA | −42.0 | 51.6 | NA | NA |
| 7 | −24.2 | −31.4 | NA | −39.4 | 12.5 | NA | NA |
| 8 | −6.7 | −7.4 | NA | −42.4 | 18.8 | NA | NA |
| 9 | 4.5 | 1.1 | NA | 7.2 | 9.2 | NA | NA |
| 10 | 2.8 | −0.2 | NA | −2.7 | 22.9 | NA | NA |
| 11 | −13.0 | −9.4 | NA | −54.0 | 44.3 | NA | NA |
| Mean | −8.9 | −13.9 | NA | −18.9 | 23.0 | NA | NA |
| p-Value | 0.0004 | 0.0001 | | 0.0371 | 0.0068 | | |
| Group B | | | | | | | |
| 1 | −19.2 | −27.1 | −24.4 | −33.4 | 20.0 | 22.3 | −81.9 |
| 2 | −32.2 | −35.7 | −28.0 | −60.4 | 4.3 | 3.2 | −25.3 |
| 3 | −21.4 | −33.6 | −35.6 | −33.4 | 30.4 | 38.6 | −17.4 |
| 4 | −19.9 | −24.6 | −15.1 | −20.8 | 9.6 | 16.1 | −27.0 |
| 5 | −3.3 | −2.1 | −29.4 | −41.1 | 5.8 | 2.4 | −22.4 |

TABLE II-continued

Patient Study Lipid Profile Data

| Pt. No | Total-C | LDL-C | Apo B | Trigs | HDL-C | HDL$_2$C | Lp(a) |
|---|---|---|---|---|---|---|---|
| 6 | | | Patient Withdrew From Study | | | | |
| 7 | 23.1 | −32.6 | −42.6 | −58.6 | 49.2 | 68.9 | −14.3 |
| 8 | 24.8 | 34.0 | −28.4 | 5.5 | 6.5 | −6.8 | NA |
| 9 | 10.1 | 12.0 | −16.8 | −11.6 | 20.7 | −12.3 | 40.6 |
| 10 | −2.9 | −7.7 | −28.0 | −59.0 | 53.1 | 70.5 | 41.2 |
| 11 | −10.5 | −18.8 | −25.3 | −53.4 | 31.8 | 39.7 | NA |
| 12 | −20.0 | −30.8 | −30.4 | 11.7 | 21.1 | 25.0 | −28.4 |
| 13 | 17.4 | 16.8 | −17.5 | −17.5 | 51.3 | 51.9 | 38.5 |
| 14 | −9.4 | −16.6 | −32.0 | −46.9 | 52.3 | 67.6 | 17.6 |
| Mean | −8.7 | −12.8 | −32.2 | −27.2 | 25.3 | 30.1 | −17.9 |
| p−Value | 0.0002 | <0.0001 | 0.0001 | <0.0001 | <0.0002 | 0.0002 | <0.0188 |
| Combined | −8.7 | −13.3 | Gp B only | −26.1 | 25.3 | Gp B only | Gp B only |
| p−Value | 0.0002 | <0.0001 | only | <.0001 | <0.0001 | only | only |

The data reported in TABLE II shows that the LDL levels in the Group A patients had a mean decrease of −13.9% and triglyceride decrease of −18.9% HDL cholesterol levels, the beneficial cholesterol, were raised by 23.0% in this Group. Similar results were obtained with the Group B patients. These studies demonstrate that dosing the sustained release formulation during the evening hours or at night provides reductions in LDL cholesterol levels equal to immediate release niacin on a milligram per milligram basis, but superior reductions in triglyceride reductions when compared to sustained release formulations dosed during daytime hours on a milligram per milligram basis. Additionally, the increases in HDL cholesterol obtained from dosing the sustained release formulation during the evening or a night were +23.0% for one group and +25.3% for the other group. Dosing during the evening therefore provides reduction in LDL cholesterol plus significant decreases in triglycerides and increases in HDL cholesterol with once-a-day dosing.

Groups A and B were also tested for liver enzymes (AST, ALT and Alkaline Phosphatase), uric acid and fasting glucose levels at the start of the study described hereinabove (to form a baseline) and at two, four and eight week intervals. The results of these tests are listed in TABLES III–VII hereinbelow.

TABLE III

THE EFFECT OF NIASPAN ® THERAPY ON AST (SGOT) LEVELS (U/L)
(1500 mgs dosed once-a-day at night)
(n = 28)
Weeks of Therapy With NIASPAN ®

| Pt # | Baseline | 2 Wks. | 4 Wks. | 8 Wks. | Reference Range |
|---|---|---|---|---|---|
| Group A | | | | | |
| 1 | 28 | 29 | 25 | 25 | 0–50 |
| 2 | 24 | 25 | 24 | 26 | 0–50 |
| 3 | 17 | 18 | 22 | 21 | 0–50 |
| 4 | 14 | 16 | 15 | 17 | 0–50 |
| 5 | 22 | NA | 32 | 52 | 0–50 |
| 6 | 21 | 17 | 17 | 14 | 0–50 |
| 7 | 17 | 17 | 14 | 18 | 0–50 |
| 8 | 20 | 21 | 22 | 22 | 0–50 |
| 9 | 16 | 16 | 17 | 20 | 0–50 |
| 10 | 18 | 21 | 21 | 25 | 0–50 |
| 11 | 21 | 21 | 22 | 21 | 0–50 |

TABLE III-continued

THE EFFECT OF NIASPAN ® THERAPY ON AST (SGOT) LEVELS (U/L)
(1500 mgs dosed once-a-day at night)
(n = 28)
Weeks of Therapy With NIASPAN ®

| Pt # | Baseline | 2 Wks. | 4 Wks. | 8 Wks. | Reference Range |
|---|---|---|---|---|---|
| Group B | | | | | |
| 1 | 23 | 25 | 38 | 33 | 0–50 |
| 2 | 20 | 20 | 21 | 21 | 0–50 |
| 3 | 15 | 20 | 18 | 19 | 0–50 |
| 4 | 25 | 22 | 25 | 26 | 0–50 |
| 5 | 23 | 21 | 17 | 18 | 0–50 |
| 6 | | PATIENT WITHDREW DUE TO FLUSHING | | | |
| 7 | 21 | 18 | 18 | 19 | 0–50 |
| 8 | 18 | 19 | 18 | 19 | 0–50 |
| 9 | 15 | 16 | 18 | 15 | 0–50 |
| 10 | 16 | 15 | 19 | 28 | 0–50 |
| 11 | 20 | 22 | 24 | 28 | 0–50 |
| 12 | 23 | 25 | 28 | 22 | 0–50 |
| 13 | 20 | 15 | 20 | 19 | 0–50 |
| 14 | 18 | 25 | 20 | 18 | 0–50 |
| Combined Mean | 19.8 | 20.4 | 20.8 | 21.1 | |
| Change From Baseline | | +3.0% | +5.1% | +6.6% | |

Level of Significance: p = 0.4141

TABLE IV

THE EFFECT OF NIASPAN ® THERAPY ON ALT (SGPT) LEVELS (U/L)
(1500 mgs dosed once-a-day at night)
(n = 28)
Weeks Of Therapy With Niaspan ®

| Pt # | Baseline | 2 Wks. | 4 Wks. | 8 Wks. | Reference Range |
|---|---|---|---|---|---|
| Group A | | | | | |
| 1 | 32 | 28 | 39 | 30 | 0–55 |
| 2 | 24 | 25 | 23 | 26 | 0–55 |
| 3 | 18 | 23 | 30 | 30 | 0–55 |
| 4 | 7 | 13 | 14 | 14 | 0–55 |
| 5 | 14 | NA | 43 | 46 | 0–55 |
| 6 | 22 | 11 | 14 | 10 | 0–55 |
| 7 | 9 | 7 | 11 | 7 | 0–55 |
| 8 | 16 | 18 | 23 | 21 | 0–55 |
| 9 | 14 | 17 | 20 | 14 | 0–55 |

TABLE IV-continued

THE EFFECT OF NIASPAN ® THERAPY ON ALT (SGPT) LEVELS (U/L)
(1500 mgs dosed once-a-day at night)
(n = 28)
Weeks Of Therapy With Niaspan ®

| Pt # | Baseline | 2 Wks. | 4 Wks. | 8 Wks. | Reference Range |
|---|---|---|---|---|---|
| 10 | 14 | 15 | 17 | 19 | 0–55 |
| 11 | 18 | 18 | 20 | 16 | 0–55 |
| Group B | | | | | |
| 1 | 16 | 17 | 27 | 29 | 0–55 |
| 2 | 16 | 14 | 15 | 22 | 0–55 |
| 3 | 13 | 21 | 13 | 16 | 0–55 |
| 4 | 23 | 20 | 26 | 17 | 0–55 |
| 5 | 21 | 23 | 17 | 15 | 0–55 |
| 6 | PATIENT WITHDREW DUE TO FLUSHING | | | | |
| 7 | 21 | 16 | 18 | 21 | 0–55 |
| 8 | 18 | 20 | 17 | 18 | 0–55 |
| 9 | 11 | 5 | 11 | 8 | 0–55 |
| 10 | 8 | 10 | 14 | 17 | 0–55 |
| 11 | 17 | 12 | 18 | 16 | 0–55 |
| 12 | 14 | 18 | 20 | 16 | 0–55 |
| 13 | 14 | NA | 11 | 10 | 0–55 |
| 14 | 23 | 23 | 19 | 19 | 0–55 |
| Combined Mean | 17.7 | 17.5 | 19.3 | 18.2 | |
| Change From Baseline | | −1.1% | 9.0% | +2.8% | |

Level of Significance: p = 0.3424

TABLE V

THE EFFECT OF NIASPAN ® THERAPY ON ALKALINE PHOSPHATE LEVELS (U/L)
0 mgs dosed once a-day at night)
(n = 28)
Weeks Of Therapy With Niaspan ®

| P.t. # | Baseline | 2 Wks. | 4 Wks. | 8 Wks. | Reference Range |
|---|---|---|---|---|---|
| Group A | | | | | |
| 1 | 52 | 56 | 57 | 55 | 20–140 |
| 2 | 103 | 100 | 89 | 102 | 20–140 |
| 3 | 54 | 45 | 53 | 51 | 20–140 |
| 4 | 70 | 68 | 71 | 91 | 20–140 |
| 5 | 77 | NA | 74 | 81 | 20–140 |
| 6 | 55 | 48 | 49 | 51 | 20–140 |
| 7 | 72 | 71 | 79 | 75 | 20–140 |
| 8 | 55 | 49 | 47 | 50 | 20–140 |
| 9 | 53 | 55 | 56 | 45 | 20–140 |
| 10 | 74 | 73 | 75 | 75 | 20–140 |
| 11 | 18 | 18 | 20 | 16 | 20–140 |
| Group B | | | | | |
| 1 | 73 | 67 | 89 | 95 | 20–140 |
| 2 | 82 | 64 | 72 | 71 | 20–140 |
| 3 | 73 | 69 | 72 | 82 | 20–140 |
| 4 | 37 | 36 | 37 | 38 | 20–140 |
| 5 | 65 | 53 | 54 | 61 | 20–140 |
| 6 | PATIENT WITHDREW DUE TO FLUSHING | | | | |
| 7 | 64 | 58 | 58 | 58 | 20–140 |
| 8 | 55 | 78 | 65 | 73 | 20–140 |
| 9 | 94 | 92 | 103 | 93 | 20–140 |
| 10 | 69 | 67 | 70 | 65 | 20–140 |
| 11 | 59 | 67 | 63 | 72 | 20–140 |
| 12 | 65 | 59 | 59 | 63 | 20–140 |
| 13 | 64 | 68 | 66 | 64 | 20–140 |
| 14 | 72 | 61 | 59 | 64 | 20–140 |
| Combined Mean | 66.5 | 61.5 | 63.3 | 65.8 | |
| Change | | −6.1% | −3.4% | +0.005% | |

TABLE V-continued

THE EFFECT OF NIASPAN ® THERAPY ON ALKALINE PHOSPHATE LEVELS (U/L)
0 mgs dosed once a-day at night)
(n = 28)
Weeks Of Therapy With Niaspan ®

| P.t. # | Baseline | 2 Wks. | 4 Wks. | 8 Wks. | Reference Range |
|---|---|---|---|---|---|
| From Baseline | | | | | |

Level of Significance: p = 0.0236

TABLE VI

THE EFFECT OF NIASPAN ® ON URIC ACID LEVELS (mg/dL)
(1500 mgs dosed once-a-day at night)
(n = 28)
Weeks Of Therapy With NIASPAN ®

| P.t. # | Baseline | 2 Wks. | 4 Wks. | 8 Wks. | Reference Range |
|---|---|---|---|---|---|
| Group A | | | | | |
| 1 | 5.2 | 5.0 | 4.8 | 4.3 | 4.0–8.5 |
| 2 | 4.0 | 4.6 | 4.5 | 6.2 | 2.5–7.5 |
| 3 | 6.3 | 7.0 | 6.5 | 6.2 | 4.0–8.5 |
| 4 | 3.1 | 4.6 | 4.2 | 3.8 | 2.5–7.5 |
| 5 | 3.4 | NA | 3.3 | 4.2 | 2.5–7.5 |
| 6 | 6.6 | 5.5 | 5.6 | 4.7 | 4.0–8.5 |
| 7 | 3.8 | 4.5 | 4.3 | 4.9 | 2.5–7.5 |
| 8 | 4.4 | 3.8 | 5.1 | 4.5 | 2.5–7.5 |
| 9 | 3.9 | 4.5 | 4.6 | 3.5 | 2.5–7.5 |
| 10 | 2.6 | 2.9 | 2.8 | 2.7 | 2.5–7.5 |
| 11 | 4.7 | 5.5 | 5.2 | 5.3 | 2.5–7.5 |
| Group B | | | | | |
| 1 | 3.7 | 4.2 | 4.7 | 3.5 | 2.5–7.5 |
| 2 | 2.8 | 3.5 | 3.6 | 2.3 | 4.0–8.5 |
| 3 | 4.2 | 5.3 | 5.5 | 5.3 | 2.5–7.5 |
| 4 | 4.7 | 3.9 | 5.1 | 3.6 | 4.0–8.5 |
| 5 | 3.7 | 4.1 | 4.1 | 3.8 | 2.5–7.5 |
| 6 | PATIENT WITHDREW DUE TO FLUSHING | | | | |
| 7 | 5.8 | 6.6 | 6.6 | 6.8 | 2.5–7.5 |
| 8 | 4.7 | 4.3 | 5.4 | 5.6 | 2.5–7.5 |
| 9 | 3.7 | 4.6 | 5.1 | 3.8 | 2.5–7.5 |
| 10 | 4.2 | 5.0 | 4.4 | 8.5 | 2.5–7.5 |
| 11 | 1.9 | 3.0 | 2.8 | 5.0 | 2.5–7.5 |
| 12 | 5.6 | 5.4 | 6.2 | 5.6 | 4.0–8.5 |
| 13 | 4.2 | 4.6 | 4.6 | 5.3 | 2.5–7.5 |
| 14 | 5.5 | 5.4 | 6.1 | 5.3 | 2.5–7.5 |
| Combined Mean | 4.54 | 4.82 | 4.92 | 4.86 | *p = 0.3450 |
| Change From Baseline | | +6.2% | +8.4% | +7.0% | |

*Level of Significance: p = 0.3450

TABLE VII

THE EFFECT OF NIASPAN ® THERAPY ON FASTING GLUCOSE LEVELS (mg/dL)
(1500 mgs dosed once-a-day at night)
(n = 28)
Weeks Of Therapy With NIASPAN ®

| P.t. # | Baseline | 2 Wks. | 4 Wks. | 8 Wks. | Reference Range |
|---|---|---|---|---|---|
| Group A | | | | | |
| 1 | 114 | 122 | 123 | 110 | 70–115 |
| 2 | 101 | 105 | 107 | 101 | 80–125 |

TABLE VII-continued

THE EFFECT OF NIASPAN ® THERAPY
ON FASTING GLUCOSE LEVELS (mg/dL)
(1500 mgs dosed once-a-day at night)
(n = 28)
Weeks Of Therapy With NIASPAN ®

| P.t. # | Baseline | 2 Wks. | 4 Wks. | 8 Wks. | Reference Range |
|---|---|---|---|---|---|
| 3 | 99 | 98 | 109 | 103 | 70–115 |
| 4 | 100 | 118 | 94 | 94 | 80–125 |
| 5 | 89 | NA | 82 | 103 | 80–125 |
| 6 | 97 | 103 | 94 | 107 | 70–115 |
| 7 | 85 | 107 | 100 | 94 | 80–125 |
| 8 | 98 | 107 | 103 | 101 | 80–125 |
| 9 | 97 | 97 | 100 | 110 | 80–125 |
| 10 | 94 | 101 | 111 | 97 | 70–115 |
| 11 | 102 | 103 | 95 | 95 | 80–125 |
| Group B | | | | | |
| 1 | 101 | 97 | 83 | 99 | 70–115 |
| 2 | 90 | 95 | 96 | 89 | 80–125 |
| 3 | 96 | 98 | 95 | 97 | 70–125 |
| 4 | 116 | 139 | 113 | 125 | 80–125 |
| 5 | 88 | 92 | 91 | 95 | 70–115 |
| 6 | PATIENT WITHDREW DUE TO FLUSHING | | | | |
| 7 | 106 | 114 | 118 | 117 | 70–115 |
| 8 | 95 | 106 | 106 | 108 | 70–115 |
| 9 | 81 | 92 | 84 | 92 | 70–115 |
| 10 | 108 | 117 | 122 | 105 | 70–115 |
| 11 | 85 | 106 | 106 | 108 | 70–115 |
| 12 | 92 | 89 | 101 | 86 | 80–125 |
| 13 | 99 | 105 | 94 | 100 | 70–125 |
| 14 | 100 | 108 | 84 | 107 | 70–125 |
| Combined Mean | 98.4 | 105.8 | 101.6 | 102.3 | |
| Change From Baseline | | +7.5% | +3.3% | +4.0% | |

Level of Significance: p = 0.0021

In order to provide a comparison between the state of the art prior to the present invention, and in order to quantify the magnitude of the improvement that the invention provides over the prior art, another study was conducted. This study included 240 patients dosed according to the present invention as described hereinabove. Compared to this group was the group of patients studied by McKenney et al., as reported hereinabove. The results of this study are reported in TABLE VIII hereinbelow.

TABLE VIII

A Comparison of Changes in Liver Function Tests

| | 0 | 500 | 1000 | 1500 | 2000 | 2500 | 3000 | TOTAL |
|---|---|---|---|---|---|---|---|---|
| McKenney SR[b] Niacin | | | | | | | | |
| AST | 23.8 | 27.9 | 40.4 | 36.6 | 56.5 | na | 97.0 | |
| % | — | 117 | 170 | 154 | 237 | na | 408 | |
| Invention Dosage[c] | | | | | | | | |
| AST | 24.3 | na | 23.7 | 27.5 | 26.6 | 27.6 | 27.8 | |
| % | — | na | 98 | 113 | 109 | 114 | 114 | |
| McKenney SR Niacin | | | | | | | | |
| AST | 25.6 | 29.5 | 36.3 | 39.0 | 59.1 | na | 100.0 | |
| % | — | 115 | 142 | 152 | 231 | na | 391 | |
| Invention Dosage | | | | | | | | |
| ALT | 21.4 | na | 18.7 | 22.6 | 21.3 | 22.4 | 21.8 | |
| % | — | na | 87 | 106 | 100 | 105 | 102 | |
| McKenney SR Niacin | | | | | | | | |
| ALK | 95 | 95 | 106 | 105 | 136 | na | 135 | |
| % | — | 100 | 112 | 111 | 143 | na | 142 | |
| Invention Dosage | | | | | | | | |
| ALK | 74.7 | na | 73.9 | 76.1 | 73.4 | 76.7 | 78.0 | |
| % | — | na | 99 | 102 | 98 | 103 | 104 | |
| McKenney SR Niacin | | | | | | | | |
| Drop | — | 0 | 2 | 2 | 7 | na | 7 | 18 |
| n | — | — | — | — | — | — | — | 23 |
| % | — | 0 | 9 | 9 | 30 | na | 30 | 78 |
| Invention Dosage | | | | | | | | |
| Drop | — | — | 0 | 0 | 0 | 0 | 0 | 0 |
| n | — | — | 26 | 67 | 97 | 35 | 15 | 240 |
| % | — | — | 0 | 0 | 0 | 0 | 0 | 0 |
| 1 year | — | — | 15 | 47 | 77 | 31 | 15 | 184 |
| 1 year | — | — | 58 | 69 | 79 | 89 | 100 | 77 |

Dosed twice-per-day as described in "A Comparison of the Efficacy and Toxic Effects of Sustained - vs. Immediate - Release Niacin in Hypercholesterolemic Patients" by McKenney et al. Journal of the American Medical Association, March 2, 1994; Vol. 271, No. 9, pages 672–677.
[b]SR is 'sustained release"
[2]Dosed once-per-day at night The results of the comparison of the studies reported in TABLE VIII show that the control group (the McKenney group) had 18 of 23, or 78 percent of the patients therein drop out of the test because of an increase in their respective liver function tests. The patients withdrew at the direction of the investigator. In comparison, a group of 240 patients treated according to the present invention had zero patients drop out, based upon the same criteria for withdrawal. The tests results reported above indicate that this sustained release dosage form caused no elevation in liver function tests (i.e. no liver damage), no elevations in uric acid and only a small, 7.5% increase in fasting glucose levels which in fact decreased during continued therapy.

Thus, it should be evident that the compositions and method of the present invention are highly effective in controlling hyperlipidemia in hyperlipidemics, by reducing the levels of LDL cholesterol, triglyceride and Lp(a) while increasing HDL cholesterol levels. The present invention is also demonstrated not to cause elevations in liver function tests, uric acid or glucose levels for the hyperlipidemics.

EXAMPLE II

In order to demonstrate the effectiveness of the pharmaceutical combinations and methods of the present invention over an antihyperlipidemia compound and method, nicotinic acid sustained release compositions coated with different HMG-CoA reductase inhibitors are prepared according to the disclosure hereinabove and hereinbelow. The composition ingredients and amounts are listed in Table IXA and IXB and the results of the study are recited in Tables X and XI hereinbelow.

TABLE IXA

Coated Tablet Composition

| Ingredient | 500 mg | 750 mg | 1000 mg |
|---|---|---|---|
| Core Tablet | — | — | — |
| Nicotinic Acid | 500 | 750 | 1000 |
| Hydroxypropyl methylcellulose (Methocel E10) | 203 | 183.1 | 157 |
| Povidone | 17.2 | 25.8 | 34.5 |
| Stearic Acid | 7.3 | 9.7 | 12.1 |
| Core Tablet Weight | 727.5 mg | 990.5 mg | 1203.6 |
| Lovastatin | 10. mg | 10 mg | 10 mg |
| Polyethylene Glycol | 0.9 mg | 0.9 mg | 0.9 mg |
| Hydroxypropyl methylcellulose (Methocel E5) | 29.1 mg | 29.1 mg | 29.1 mg |
| Coating Weight | 40 mg | 40 mg | 40 mg |
| Total Tablet Weight | 767.5 | 1030.5 | 1243.6 |

TABLE IXB

Batch Formulation

| | Niacin 750 mg Lovastatin 10 mg | | Niacin 1000 mg Lovastatin 10 mg | |
|---|---|---|---|---|
| Material | Per Unit MG/Tablet | Per Batch, G | Per Unit MG/Tablet | Per Batch, G |
| Lovastatin | 10.0 | 80.54 | 10.0 | 64.74 |
| Methocel E5 Premium, LV | 29.1 | 234.35 | 19.4 | 125.60 |
| Pluracol E1450 | 0.9 | 7.25 | 0.6 | 3.88 |
| Purified Water | na | 2899.26 | na | 1942.20 |
| Coating Suspension Total | na | 3221.4 | na | 2136.42 |
| Niacin 750 mg | 968.5 | 6000.0 | 1203.6 | 6000.0 |
| Core Tablet Total | 1008.5 | 9221.4 | 1233.6 | 8136.42 |

The core tablet ingredients are compounded together to form sustained release tablets, as described in Example I. The sustained release tablets are then coated as follows. The lovastatin, Methocel E5 and Pluracol E1450 are pre-blended in a polyethylene bag for about 2–3 minutes. The mixture is then passed through a 710 mm sieve. A low sheer propeller blade mixer is positioned in a stainless steel beaker containing purified water, USP. The mixer speed is adjusted until a vortex forms. The blended mixture in the polyethylene bag is slowly added to the purified water. If necessary, the mixer speed should be adjusted during the addition of the dry mixture so that the vortex conditions are maintained. Continue mixing until the blended material is completely dispersed.

Place the stainless steel beaker on a balance and record gross weight. Calculate net weight of coating suspension as follows:

Net weight of coating suspension=gross weight of coating suspension−beaker tare weight Following manufacture of the coating suspension, the sustained release tablets are coated as follows. The Hicoater HCT 48/60 tablet coating machine is first cleaned appropriately pursuant to SOP FM700-Procedure for the cleaning of Hicoater HCT 48/60 tablet coating machine. The Hicoater HCT 48/60 tablet coating machine should be equipped with a 9 liter pan, 0.6 cc gear prop, single gun spray bar, 2.5 mm cap and 1.5 mm nozzle port.

Following SOP FM500—Procedure for the operators of the Hicoater HCT 48/60 tablet coating machine in manual mode, the atomization air pressure should be set to 150 liter/min and the pattern air pressure should be set to 100 liters/min. Once the atomization air pressure and the pattern air pressure are set, the coating suspension is placed on a balance and the suspension feed fine is placed in the coating suspension. The suspension return line is then placed in another container. The low sheer mixer is then placed in the coating suspension and the mixing is started. A period of about 60 minutes should be allowed before proceeding to the next step.

After about 60 minutes, the suspension pump and purge lines are switched on. When the lines are filled with coating suspension, relocate the suspension return line to the coating suspension container. The solution following through the guns should be set to about 40 g/min according to SOP FM500.

Next, the batch of nicotinic acid sustained release tablets are loaded into the coating machine. Close the glass door on the machine. Start the inlet and exhaust air blowers. Adjust the inlet and exhaust air blower until air flow is 170(±20)cfm and pan pressure negative is between—½ inch and 1 inch.

Coat the tablets as follows. Set the pan to JOG at 3.3 rpm, 5 seconds on and 30 seconds off. Switch on the inlet air heater and adjust to 60° C. Proceed to the film coating phase where the exhaust air temperature reaches 40° C. To further coat, set the pan to run. Increase the pan speed to 15 rpm and start the spray. Calculate the coating end point or target coated tablet weight as follows:

Coating end point (750 mg)=Starting tablet weight, mg×1.0413 for 750 mg tablets

Coating end point (1000 mg)=Starting tablet weight, mg×1.0249 for 1000 mg tablets Coating end point (500 mg)=Starting tablet weight, mg×1.0643 for 500 mg tablets The coating end point should be approximately ±10% of the target coated tablet weight range.

Continue to apply coating suspension until the end point is reached. Proceed to the next step, which is cooling upon reaching the end point.

To cool, stop the spray. Set the pan to JOG at 3.3 rpm. Switch off the inlet air heat and allow the coated tablets to cool to approximately 35° C. Stop the pan and turn off the inlet and exhaust blowers.

To discharge, use the JOG button on the front of the machine to turn the pan until the trap door is above the surface of the product bed. Position a tared double polyethylene lined container with desiccant present in the outer bag beneath the discharge chute. Open the trap door. Rotate the JOG button until coated tablets begin to discharge. Continue to rotate the pan until all the product is discharged from the pan. Stop the pan and remove the container. Then weigh the coated sustained release tablets.

EXAMPLE III

A study group consisting of 382 patients was formed. Blood samples were taken from the patients, and were tested for total cholesterol, LDL-cholesterol, triglycerides and HDL-cholesterol to establish baseline levels from which fluctuations in these lipids could be composed. The patients were then placed upon a regimen as follows: Of the 382 patients, 258 patients took approximately 2000 mg of Niaspan®, once per day before going to bed, and 122 of 124 patients took concomitantly, once per day at night before going to bed, approximately 2000 mg of Niaspan® (two Niaspan® 1000 mg tablets) and one HMG-CoA reductase inhibitor tablet, as reported in Table X. More specifically, 4 patients took two Niaspan® 1000 mg tablets and one fluvastatin 20 mg tablet at the same time once per day at bedtime; 12 patients took two Niaspan® 1000 mg tablets one lovastatin 20 mg tablet at the same time once per day at night before going to bed; 69 patients took two Niaspan® 1000 mg tablets and one pravastatin 20 mg tablet at the same time once per day at night before going to bed; 27 patients took two Niaspan® 1000 mg tablets and one simvastatin 10 mg tablet at the same time once per day at night before going to bed; and 10 patients took two Niaspan® 1000 mg tablets and one HMG-CoA reductase tablet at the same time once per day at night before going to bed. However, during the study, these 10 patients changed between different HMG-CoA reductase inhibitors. Nevertheless, the particular HMG-CoA reductase inhibitors taken by these 10 patients were those recited in Table X.

After treatment, with a mean treatment duration of approximately 43 weeks, the lipid profiles of the patients were again tested. The results of the tests conducted, showing the change in the lipid profiles as percentage change from the baseline, are reported in Tables X and XI hereinbelow. The results of the tests conducted, showing the change in clinical chemistry profiles as percentage change from baseline, are reported in Table XII hereinbelow, and showing the number of patients and the % of the total patients in the study that recorded elevations above upper limits of normal (ULN) for selected clinical chemistry parameters, are reported in Tables XIII and XIV hereinbelow.

No incidences or symptoms of myopathy or rhabdomyolysis were described by or observed in the 122 individuals receiving the combination therapy pursuant to this Example III.

TABLE X

NIASPAN ® AND NIASPAN ® /HMG-CoA REDUCTASE INHIBITOR LONG-TERM STUDY EFFICACY DATA:
MEAN TREATMENT DURATION - ABOUT 43 WEEKS
% Change from Baseline

| | N | TC | LDL-C | HDL-C | TG | Niaspan ® | Statin |
|---|---|---|---|---|---|---|---|
| Niaspan ® | 258 | −12.4 | −19.1 | +26.0 | −25.5 | 2000 | — |
| Niaspan ® + Statin Total | 122 | −23.8 | −31.8 | +27.7 | −32.5 | 2000 | — |
| Fluvastatin | 4 | −22.1 | −31.8 | +29.3 | −30.3 | 2000 | 20 |
| Lovastatin | 12 | −20.9 | −28.2 | +23.5 | −23.8 | 2000 | 20 |
| Pravastatin | 69 | −23.7 | −31.4 | +26.5 | −34.5 | 2000 | 20 |
| Simvastatin | 27 | −24.9 | −33.0 | +33.9 | −36.4 | 2000 | 10 |
| Multiple | 10 | −25.3 | −35.1 | +23.7 | −19.8 | 2000 | — |

Table XI also reports results of the tests conducted. More specifically, Table XI reports complete efficacy data (lipid results) for 53 of the 124 patients, who took concomitantly, once per day at night before going to bed, Niaspan® and an HMG-CoA reductase inhibitor, as indicated above in this Example III. Table XI further reports complete efficacy data (lipid results) for 16 patient, who took concomitantly, once per day at night before going to bed, Niaspan® and BAS, a bile acid sequestrant (i.e., cholestyramine or colestipol). Table XI also reports complete efficacy data (lipid results) for 15 patients, who took concomitantly, once per day at night before going to bed, Niaspan®, BAS (a bile acid sequestrant, i.e., cholestyramine or colestipol), and an HMG-CoA reductase inhibitor.

TABLE XI

LIPID RESULTS
Mean Percentage Change from Baseline
LONG TERM POPULATION

| | | n | Subgroup Total | | Niaspan* Only | | Niaspan* + HmgCoA | | Niaspan* + BAS | | Niaspan* + Both |
|---|---|---|---|---|---|---|---|---|---|---|---|
| | | | | | | Total # of Patients | | | | | |
| | | | 269 | | 185 | | 53 | | 16 | | 15 |
| LDL (mg/dL) | Baseline | 269 | 201.0 ± 1.9 | 181 | 198.2 ± 2.1 | 53 | 208.0 ± 4.7 | 16 | 207.1 ± 11.1 | 15 | 203.7 ± 8.8 |
| | 12 weeks | 234 | (−10.7 ± 0.84)** | 150 | (−11.4 ± 1.03)** | 53 | (−8.6 ± 1.85)** | 16 | (−11.2 ± 3.42)** | 15 | (−10.3 ± 3.32)** |
| | 24 weeks | 208 | (−14.5 ± 0.98)** | 126 | (−13.4 ± 1.16)** | 52 | (−16.0 ± 2.43)** | 16 | (−14.8 ± 3.24)** | 14 | (−18.2 ± 2.53)** |
| | 48 weeks | 174 | (−21.5 ± 1.10)** | 101 | (−17.7 ± 1.28)** | 45 | (−31.7 ± 2.12)** | 15 | (−19.5 ± 3.73)** | 13 | (−18.6 ± 3.50)** |
| | 72 weeks | 140 | (−23.2 ± 1.19)** | 79 | (−18.1 ± 1.52)** | 39 | (−31.6 ± 1.73)** | 9 | (−30.9 ± 3.83)** | 13 | (−24.0 ± 4.12)** |
| | 96 weeks | 130 | (−23.8 ± 1.37)** | 73 | (−17.5 ± 1.65)** | 37 | (−32.2 ± 2.32)** | 7 | (−27.8 ± 4.19)** | 13 | (−33.0 ± 4.18)** |
| HDL (mg/dL) | Baseline | 269 | 43.4 ± 0.6 | 185 | 43.6 ± 0.7 | 53 | 42.7 ± 1.4 | 16 | 42.5 ± 2.3 | 15 | 44.0 ± 2.2 |
| | 12 weeks | 234 | (19.6 ± 1.09)** | 150 | (20.2 ± 1.36)** | 53 | (15.1 ± 2.16)** | 16 | (31.1 ± 4.40)** | 15 | (17.3 ± 3.83)** |
| | 24 weeks | 208 | (24.9 ± 1.31)** | 126 | (25.1 ± 1.74)** | 52 | (22.5 ± 2.37)** | 16 | (38.7 ± 3.02)** | 14 | (16.4 ± 5.09)** |
| | 48 weeks | 174 | (27.9 ± 1.56)** | 101 | (29.0 ± 2.05)** | 45 | (22.8 ± 3.07)** | 15 | (36.2 ± 5.25)** | 13 | (17.6 ± 4.74)** |
| | 72 weeks | 140 | (25.8 ± 1.54)** | 79 | (27.8 ± 2.15)** | 39 | (22.2 ± 2.57)** | 9 | (37.4 ± 6.31)** | 13 | (16.5 ± 3.44)** |
| | 96 weeks | 130 | (29.1 ± 1.68)** | 73 | (32.1 ± 2.46)** | 37 | (24.7 ± 2.36)** | 7 | (31.2 ± 9.44)** | 13 | (23.2 ± 4.00)** |

TABLE XI-continued

LIPID RESULTS
Mean Percentage Change from Baseline
LONG TERM POPULATION

| | Subgroup | n | Total | | Niaspan* Only | | Niaspan* + HmgCoA | | Niaspan* + BAS | | Niaspan* + Both | |
|---|---|---|---|---|---|---|---|---|---|---|---|---|
| | | | | | | | Total # of Patients | | | | | |
| | | | 269 | | 185 | | 53 | | 16 | | 15 | |
| Total Cholesterol (mg/dL) | Baseline | 269 | 276.0 ± 2.1 | 185 | 273.0 ± 2.4 | 53 | 285.2 ± 4.9 | 16 | 282.0 ± 10.6 | 15 | 272.8 ± 9.1 | |
| | 12 weeks | 234 | (−7.2 ± 0.63)** | 150 | (−7.4 ± 0.76)** | 53 | (−6.9 ± 1.50)** | 16 | (−6.3 ± 2.23)** | 15 | (−7.0 ± 2.47)* | |
| | 24 weeks | 208 | (−9.2 ± 0.6)** | 126 | (−7.8 ± 0.88)** | 52 | (−11.8 ± 1.92)** | 16 | (−8.2 ± 2.20)** | 14 | (−13.7 ± 1.96)** | |
| | 48 weeks | 174 | (−14.0 ± 0.87)** | 101 | (−10.5 ± 0.94)** | 45 | (−23.1 ± 1.77)** | 15 | (−11.3 ± 2.82)** | 13 | (−13.4 ± 2.42)** | |
| | 72 weeks | 140 | (−15.7 ± 0.97)** | 79 | (−11.4 ± 1.15)** | 39 | (−24.1 ± 1.41)** | 9 | (−13.9 ± 4.51)** | 13 | (−18.2 ± 2.99)** | |
| | 96 weeks | 130 | (−15.5 ± 1.10)** | 73 | (−10.0 ± 1.15)** | 37 | (−23.8 ± 2.05)** | 7 | (−15.1 ± 2.62)** | 53 | (−23.1 ± 3.45)** | |
| Triglycerides (mg/dL) | Baseline | 269 | 157.7 ± 4.1 | 185 | 155.9 ± 5.0 | 53 | 172.2 ± 9.3 | 16 | 161.5 ± 17.7 | 15 | 124.8 ± 11.0 | |
| | 12 weeks | 234 | (−21.1 ± 1.80)** | 150 | (−20.8 ± 2.32)** | 53 | (−23.4 ± 3.78)** | 16 | (−19.3 ± 6.32)** | 15 | (−18.9 ± 6.24)** | |
| | 24 weeks | 208 | (−21.7 ± 2.13)** | 126 | (−20.9 ± 2.65)** | 52 | (−23.5 ± 4.34)** | 16 | (−20.3 ± 7.98)* | 14 | (−23.8 ± 10.4)* | |
| | 48 weeks | 174 | (−24.2 ± 2.50)** | 101 | (−23.5 ± 2.91)** | 45 | (−30.4 ± 6.05)** | 15 | (−12.7 ± 9.78) | 13 | (−22.2 ± 6.27)** | |
| | 72 weeks | 140 | (−28.1 ± 2.75)** | 79 | (−26.5 ± 3.67)** | 39 | (−37.4 ± 3.53)** | 9 | (−1.6 ± 20.7) | 13 | (−28.7 ± 5.71)** | |
| | 96 weeks | 130 | (−25.8 ± 2.86)** | 73 | (−26.4 ± 3.80)** | 37 | (32.2 ± 4.10)** | 7 | (−5.13 ± 21.4) | 13 | (−20.5 ± 8.32)* | |
| VLDL (mg/dL) | Baseline | 269 | 31.6 ± 0.8 | 185 | 31.2 ± 1.0 | 53 | 34.4 ± 1.9 | 16 | 32.4 ± 3.5 | 15 | 25.0 ± 2.2 | |
| | 12 weeks | 234 | −(21.2 ± 1.80)** | 150 | (−20.6 ± 2.35)** | 53 | (−23.8 ± 3.61)** | 16 | (−20.0 ± 6.23)** | 15 | (−18.7 ± 6.31)** | |
| | 24 weeks | 208 | (−21.7 ± 1.80)** | 126 | (−20.9 ± 2.69)** | 52 | (−23.7 ± 4.30)** | 16 | (−20.4 ± 7.98)* | 14 | (−23.9 ± 10.4)* | |
| | 48 weeks | 174 | (−24.0 ± 2.58)** | 101 | (−23.4 ± 2.91)** | 45 | (−29.4 ± 6.57)** | 15 | (−13.3 ± 9.80) | 13 | (−22.5 ± 6.35)** | |
| | 72 weeks | 140 | (−27.2 ± 3.14)** | 79 | (−26.2 ± 3.65)** | 39 | (−37.4 ± 3.53)** | 9 | (10.5 ± 31.0) | 13 | (−28.6 ± 5.70)** | |
| | 96 weeks | 130 | (−25.8 ± 2.86)** | 73 | (−25.8 ± 3.85)** | 37 | (−32.0 ± 4.12)** | 7 | (−1.7 ± 22.4) | 13 | (−20.6 ± 8.09)* | |
| TC to HDL Ratio | Baseline | 269 | 6.63 ± 0.09 | 185 | 6.52 ± 0.10 | 53 | 6.99 ± 0.23 | 16 | 6.96 ± 1.51 | 15 | 6.40 ± 0.34 | |
| | 12 weeks | 234 | (−21.0 ± 0.88)** | 150 | (−21.6 ± 1.08)** | 53 | (−18.0 ± 1.81)** | 16 | (−27.1 ± 3.26)** | 15 | (−19.4 ± 3.87)** | |
| | 24 weeks | 208 | (−25.9 ± 0.99)** | 126 | (−24.8 ± 1.21)** | 52 | (−26.7 ± 2.25)** | 16 | (−3.34 ± 2.48)** | 14 | (−24.0 ± 4.03)** | |
| | 48 weeks | 174 | (−31.3 ± 1.13)** | 101 | (−29.1 ± 1.32)** | 45 | (−37.5 ± 2.37)** | 15 | (−33.0 ± 4.18)** | 13 | (−24.5 ± 4.61)** | |
| | 72 weeks | 140 | (−31.8 ± 1.15)** | 79 | (−29.4 ± 1.51)** | 39 | (−36.9 ± 1.87)** | 9 | (−36.0 ± 5.32)** | 13 | (−28.7 ± 4.21)** | |
| | 96 weeks | 130 | (−33.4 ± 1.16)** | 73 | (−30.1 ± 1.64)** | 37 | (−38.4 ± 1.82)** | 7 | (−33.5 ± 3.85)** | 13 | (−37.2 ± 3.10)** | |
| LDL to HDL Ratio | Baseline | 269 | 4.85 ± 0.08 | 185 | 4.75 ± 0.08 | 53 | 5.12 ± 0.20 | 16 | 5.16 ± 0.47 | 15 | 4.80 ± 0.31 | |
| | 12 weeks | 234 | (−23.7 ± 1.14)** | 150 | (−24.7 ± 1.29)** | 53 | (−19.2 ± 2.12)** | 16 | (−31.2 ± 3.94)** | 15 | (−21.8 ± 4.50)** | |
| | 24 weeks | 208 | (−29.9 ± 1.14)** | 126 | (−29.0 ± 1.42)** | 52 | (−29.8 ± 2.59)** | 16 | (−38.2 ± 3.06)** | 14 | (−28.0 ± 3.94)** | |
| | 48 weeks | 173 | (−36.8 ± 1.30)** | 100 | (−34.5 ± 1.58)** | 45 | (−43.6 ± 2.54)** | 15 | (−38.7 ± 4.61)** | 13 | (−28.6 ± 5.44)** | |
| | 72 weeks | 140 | (−37.6 ± 1.32)** | 79 | (−34.3 ± 1.77)** | 39 | (−42.9 ± 2.08)** | 9 | (−49.4 ± 2.66)** | 13 | (−33.5 ± 5.19)** | |
| | 96 weeks | 130 | (−39.8 ± 1.37)** | 73 | (−35.8 ± 1.92)** | 37 | (−45.0 ± 2.22)** | 7 | (−44.3 ± 3.62)** | 13 | (−45.3 ± 3.80)** | |
| Apolipopritein B (mg/dL) | Baseline | 244 | 148.1 ± 1.23 | 165 | 145.7 ± 1.41 | 48 | 155.8 ± 2.85 | 16 | 149.3 ± 6.03 | 15 | 149.2 ± 4.53 | |
| | 12 weeks | 138 | (−9.8 ± 1.02)** | 76 | (−11.5 ± 1.38)** | 37 | (−6.2 ± 2.06)** | 13 | (−11.4 ± 2.90)** | 12 | (−8.0 ± 2.82)** | |
| | 24 weeks | 133 | (−14.0 ± 1.06)** | 71 | (−12.6 ± 1.37)** | 36 | (−16.1 ± 2.56)** | 14 | (−13.7 ± 2.28)** | 12 | (−16.6 ± 2.48)** | |
| | 48 weeks | 123 | (−18.7 ± 1.14)** | 70 | (−15.4 ± 1.33)** | 30 | (−26.2 ± 2.60)** | 11 | (−19.2 ± 3.14) | 12 | (−18.5 ± 3.44)** | |
| | 72 weeks | 43 | (−20.2 ± 1.85)** | 31 | (−16.0 ± 1.95)** | 11 | (−32.2 ± 2.22)** | 0 | — | 1 | (−19.3) | |
| | 96 weeks | 0 | — | 0 | — | 0 | — | 0 | — | 0 | — | |
| Lp(a) (mg/dL) | Baseline | 244 | 36.7 ± 2.22 | 165 | 36.0 ± 2.64 | 48 | 34.4 ± 5.29 | 16 | 49.6 ± 8.95 | 15 | 38.5 ± 9.33 | |
| | 12 weeks | 139 | (−27.5 ± 2.19)** | 78 | (−28.8 ± 2.69)** | 36 | (−28.7 ± 4.44)** | 13 | (−28.2 ± 6.01)** | 12 | (−14.9 ± 10.9) | |
| | 24 weeks | 133 | (−28.7 ± 2.29)** | 72 | (−30.4 ± 2.70)** | 35 | (−28.0 ± 5.31)** | 14 | (−29.8 ± 5.99)** | 12 | (−19.5 ± 10.0) | |
| | 48 weeks | 131 | (−29.3 ± 4.66)** | 74 | (−36.3 ± 2.73)** | 32 | (−19.2 ± 17.6)** | 12 | (−24.0 ± 5.85)** | 13 | (−19.0 ± 7.01)* | |
| | 72 weeks | 44 | (−33.0 ± 3.84)** | 29 | (−31.5 ± 4.84)** | 12 | (−38.4 ± 7.41)** | 0 | — | 3 | (−24.7 ± 12.6) | |
| | 96 weeks | 0 | — | 0 | — | 0 | — | 0 | — | 0 | − | |

Note:
The — indicates that no measurements have been collected for that visit. Observed Values ± S.E. (percent change ± S.E). Individual data are provided on ZIP diskette.
*Significant at p ≦ 0.05, ** significant at p ≦ 0.01; matched-pair test Table XII reports clinical chemistry parameters (liver function) for all 124 patients, who took concomitantly, once per day at night before going to bed, Niaspan® and an HMG-CoA reductase inhibitor. Table XII further reports clinical chemistry parameters (liver function) for 22 patients, who took concomitantly, once per day at night before going to bed, Niaspan® and BAS (a bile acid sequestrant, i.e., cholestyramine or colestipol). Table XII also reports clinical chemistry parameters (liver function) for 17 patients who took concomitantly, once per day at night before going to bed, Niaspan®, BAS (a bile acid sequestrant, i.e., cholestyramine or colestipol), and an HMG-CoA reductase inhibitor.

TABLE XII

CHEMISTRY PARAMETERS
MEAN PERCENT CHANGE FROM BASELINE
LONG TERM POPULATION

| | n | LT Total Mean ± S.E. | n | Niaspan Only Mean ± S.E. | n | Niaspan & HMG-CoA Mean ± S.E. | n | Niaspan & BAS Mean ± S.E. | n | Niaspan & Both Mean ± S.E. |
|---|---|---|---|---|---|---|---|---|---|---|
| Total Patients | | 617 | | 454 | | 124 | | 22 | | 17 |
| AST (mIU/mL) | | | | | | | | | | |
| Baseline | 617 | 18.9 ± 0.22 | 454 | 18.7 ± 0.26 | 124 | 19.1 ± 0.44 | 22 | 20.5 ± 1.09 | 17 | 20.4 ± 1.26 |
| 12 weeks | 312 | (13.5 ± 1.54)** | 352 | (13.6 ± 1.72)** | 121 | (11.3 ± 2.78)** | 22 | (25.9 ± 16.89) | 17 | (11.4 ± 4.35)* |
| 48 weeks | 376 | (18.8 ± 2.18)** | 240 | (17.9 ± 3.00)** | 101 | (21.5 ± 3.53)** | 20 | (17.8 ± 5.07)** | 15 | (16.6 ± 9.14) |
| 96 weeks | 133 | (15.4 ± 2.96)** | 76 | (13.8 ± 4.89)** | 37 | (18.2 ± 3.36)** | 7 | (9.2 ± 3.67)** | 13 | (19.6 ± 3.16)** |
| ALT (mIU/mL) | | | | | | | | | | |
| Baseline | 617 | 23.5 ± 0.39 | 454 | 23.4 ± 0.48 | 124 | 24.3 ± 0.73 | 22 | 23.0 ± 2.08 | 17 | 19.4 ± 1.66 |
| 12 weeks | 513 | (1.8 ± 1.51) | 353 | (2.6 ± 1.84) | 121 | (−0.9 ± 2.66) | 22 | (6.7 ± 11.47) | 17 | (−1.3 ± 5.70) |
| 48 weeks | 376 | (5.7 ± 2.21)** | 240 | (3.9 ± 2.82) | 101 | (8.9 ± 4.26)* | 20 | (3.6 ± 5.74) | 15 | (16.8 ± 12.50) |
| 96 weeks | 132 | (5.7 ± 3.50) | 75 | (1.0 ± 5.41) | 37 | (10.9 ± 5.09)* | 7 | (−0.2 ± 8.19) | 13 | (21.4 ± 6.49) |
| Alk > Ph. (mlU/mL) | | | | | | | | | | |
| Baseline | 617 | 69.9 ± 0.70 | 454 | 66.0 ± 0.83 | 124 | 67.0 ± 1.56 | 22 | 59.2 ± 2.30 | 17 | 63.6 ± 3.29 |
| 12 weeks | 513 | (−0.3 ± 0.55) | 353 | (−0.6 ± 0.70) | 121 | (−0.8 ± 0.93) | 22 | (4.8 ± 2.64) | 17 | (1.3 ± 3.36) |
| 48 weeks | 375 | (0.8 ± 0.79) | 239 | (0.8 ± 1.00) | 101 | (−0.4 ± 1.19) | 20 | (1.9 ± 5.28) | 15 | (7.8 ± 4.87) |
| 96 weeks | 132 | (1.6 ± 1.20) | 75 | (2.5 ± 1.71) | 37 | (−2.0 ± 1.43) | 7 | (3.2 ± 4.19) | 13 | (6.2 ± 5.10) |
| LDH (mIU/ML) | | | | | | | | | | |
| Baseline | 617 | 147.90 ± 0.92 | 454 | 147.3 ± 1.04 | 124 | 148.4 ± 1.96 | 22 | 152.3 ± 7.03 | 17 | 156.5 ± 6.80 |
| 12 weeks | 513 | (9.7 ± 0.54)** | 353 | (9.9 ± 0.66)** | 121 | (8.2 ± 1.07)** | 22 | (14.0 ± 3.23)** | 17 | (10.8 ± 2.27)** |
| 48 weeks | 326 | (15.2 ± 0.76)** | 240 | (14.5 ± 0.93)** | 101 | (16.1 ± 1.59)** | 20 | (21.6 ± 3.63)** | 15 | (12.8 ± 2.40)** |
| 96 weeks | 133 | (17.9 ± 1.04)** | 76 | (17.1 ± 1.23)** | 37 | (20.4 ± 2.51)** | 7 | (16.8 ± 2.68)** | 13 | (16.1 ± 2.97)** |
| Total Bili.(mg/dL) | | | | | | | | | | |
| Baseline | 617 | 0.54 ± 0.010 | 454 | 0.53 ± 0.011 | 124 | 0.58 ± 0.022 | 22 | 0.65 ± 0.069 | 17 | 0.53 ± 0.039 |
| 12 weeks | 512 | (1.6 ± 1.33) | 352 | (1.5 ± 1.67) | 121 | (−0.2 ± 2.46) | 22 | (1.3 ± 4.84) | 17 | (17.1 ± 7.03)* |
| 48 weeks | 376 | (9.3 ± 1.81)** | 240 | (7.6 ± 2.26)** | 101 | (10.5 ± 3.17)** | 20 | (13.1 ± 8.84) | 15 | (24.3 ± 12.55) |
| 96 week | 132 | (15.1 ± 3.22)** | 75 | (6.0 ± 4.22) | 37 | (25.5 ± 5.20)** | 7 | (26.3 ± 11.49) | 13 | (32.2 ± 12.31)* |
| Dir.Bili. (mg/dL) | | | | | | | | | | |
| Baseline | 617 | 0.12 ± 0.002 | 454 | 0.12 ± 0.002 | 124 | 0.12 ± 0.004 | 22 | 0.13 ± 0.013 | 17 | 0.10 ± 0.007 |
| 12 weeks | 513 | (8.7 ± 1.47)** | 353 | (8.1 ± 1.76)** | 121 | (8.7 ± 3.06)** | 22 | (10.2 ± 6.50) | 17 | (18.0 ± 8.62) |
| 48 weeks | 376 | (26.4 ± 6.66)** | 240 | (26.6 ± 10.24)** | 101 | (24.4 ± 4.23)** | 20 | (24.1 ± 7.68)** | 15 | (40.1 ± 12.24)** |
| 96 weeks | 132 | (27.2 ± 3.52)** | 75 | (17.8 ± 4.22)** | 37 | (40.6 ± 6.77)** | 7 | (16.7 ± 7.66) | 13 | (49.0 ± 14.36)** |
| Amylase (mg/dL) | | | | | | | | | | |
| Baseline | 617 | 51.2 ± 0.78 | 454 | 51.2 ± 0.92 | 124 | 52.2 ± 1.72 | 22 | 49.3 ± 3.70 | 17 | 45.6 ± 3.20 |
| 12 Weeks | 513 | (6.4 ± 0.84)** | 353 | (7.2 ± 1.07)** | 121 | (4.9 ± 1.59)** | 22 | (4.1 ± 2.19) | 17 | (3.4 ± 3.39) |
| 48 weeks | 376 | (8.6 ± 1.07)** | 240 | (8.7 ± 1.34)** | 101 | (8.6 ± 1.90)** | 20 | (7.2 ± 5.23) | 15 | (10.1 ± 7.06) |
| 96 weeks | 132 | (5.3 ± 2.00)** | 75 | (5.4 ± 2.32)* | 37 | (6.6 ± 5.23) | 7 | (3.1 ± 3.58) | 13 | (2.6 ± 3.55) |

Note:
Values are based upon two different central laboratories; thus, the Baseline observed value is presented for descriptive purposes only.
*Significant at $p \leq 0.05$ **Significant at $p \leq 0.01$ Matched-pair test.
**Observed Value ± S.E. for Baseline (mean percent change from Baseline ± S.E. for Weeks 12, 48 and 96).

In Tables X–XII positive numbers reflect percentage increases and negative numbers reflect percentage decreases.

Table XIII reports the number of patients and the % of the total patients in the study that recorded elevations above upper limits of normal (ULN) for selected clinical chemistry parameters. More particularly, Table XIII reports the number of patients and the % of the 124 patients, who took concomitantly, once per day at night before going to bed, Niaspan® and an HGM-CoA reductase inhibitor, that recorded elevations above ULN for selected clinical chemistry parameters. Table XIII further reports the number of patients and the % of the 22 patients, who took concomitantly, once per day at night before going to bed, Niaspan® and BAS (a bile acid sequestrant, i.e., cholestyramine or colestipol), that recorded elevations above ULN for selected clinical chemistry parameters. Table XIII further reports the number of patients and the % of the 17 patients, who took concomitantly, once per day at night before going to bed, Niaspan®, BAS (a bile acid sequestrant, i.e., cholestyramine or colestipol), and an HMG-CoA reductase inhibitor, that recorded elevations above ULN for selected clinical chemistry parameters.

TABLE XIII

TREATMENT EMERGENT ABNORMALITIES IN SELECTED CHEMISTRY PARAMETERS LONG TERM POPULATION

| | | LT Total[1] | Niaspan ® Only | Niaspan ® & HMG-CoA Total Patients | Niaspan ® & BAS | Niaspan ® & Both |
|---|---|---|---|---|---|---|
| | | 617 | 454 | 124 | 22 | 17 |
| AST | >Normal | 70 (11%) | 44 (10%) | 17 (14%) | 5 (23%) | 4 (24%) |
| (mIU/mL) | >1.3xULN | 28 (5%) | 17 (4%) | 6 (5%) | 3 (14%) | 2 (12%) |
| | >2XULN | 5 (1%) | 3 (<1%) | 1 (<1%) | 1 (6%) | 0 |
| | >3XULN | 1 (<1%) | 1 (<1%) | 0 | 0 | 0 |
| ALT | >Normal | 44 (7%) | 23 (5%) | 14 (11%) | 2 (9%) | 5 (29%) |
| (mIU/mL) | >1.3xULN | 15 (2%) | 4 (<1%) | 5 (4%) | 2 (9%) | 4 (24%) |
| | >2xULN | 3 (<1%) | 1 (<1%) | 2 (2%) | 0 | 0 |
| | >3xULN | 1 <(1%) | 0 | 1 (<1%) | 0 | 0 |
| Alk. Phos. | >Normal | 17 (3%) | 9 (2%) | 3 (2%) | 2 (9%) | 3 (18%) |
| (mIU/mL) | >1.3xULN | 3 (1%) | 0 | 2 (2%) | 1 (5%) | 0 |
| LDH | >Normal | 94 (15%) | 60 (13%) | 23 (19%) | 8 (36%) | 3 (18%) |
| (mIU/mL) | >1.3xULN | 6 (<1%) | 4 (<1%) | 1 (<1%) | 0 | 1 (6%) |
| Fasting Glue | >Normal | 111 (18%) | 67 (15%) | 36 (28%) | 4 (18%) | (24%) |
| (mg/dL) | >1.3xULN | 6 (<1%) | 3 (<1%) | 3 (2/%) | 0 | 0 |
| Uric Acid | >Normal | 89 (14%) | 49 (11%) | 28 (23%) | 7 (32%) | 5 (29%) |
| (mIU/mL) | >1.3xULN | 5 (<1%) | 3 (<1%) | 1 (<1%) | 0 | 1 (6%) |
| Total Bili | >Normal | 10 (2%) | 5 (1%) | 4 (3%) | 0 | 1 (6%) |
| (mg/dL) | >1.3xULN | 2 (<1%) | 1 (<1%) | 1 (<1%) | 0 | 0 |
| Amylase | >Normal | 18 (3%) | 11 (2%) | 7 (6%) | 0 | 0 |
| (mg/dL) | >1.3xULN | 6 (<1%) | 5 (1%) | 1 (<1%) | 0 | 0 |
| | >2xULN | 1 (<1%) | 1 (<1%) | 0 | 0 | 0 |
| Phosphorus | <Normal | 159 (26%) | 96 (21%) | 47 (38%) | 9 (41%) | 7 (41%) |
| (mg/dL) | <2.0 mg/dL | 19 (3%) | 14 (3%) | 4 (3%) | 1 (5%) | 0 |

Note:
Percentages are calculated from the total number of patients in each column.
Abnormal liver test results for Patient 3512 are not included in this table as the data were collected at a local hospital. Refer to the initial Safety Update (Vol. I, ¶. 12-13,37)

Table XIV reports the number of patients and the % of the total patients in the study that recorded elevations 2 or 3 times above upper limits of normal (ULN) for the AST and ALT clinical chemistry parameters. More particularly, Table XIV reports the number of patients and the % of the 124 patients, who took concomitantly, once per day at night before going to bed, Niaspan and an HMG-CoA reductase inhibitor, that recorded elevations which were 2 or 3 times above ULN for the AST and ALT clinical chemistry parameters. Table XIV is consistent with that reported in Table XIII.

TABLE XIV

LONG-TERM STUDY SAFETY DATA LIVER FUNCTION TESTS

| | Niaspan ® N = 454* | Niaspan ® + HMG-CoA Reductase Inhibitor N = 124** |
|---|---|---|
| AST > 2xULN | 3 (<1%) | 1 (<1%) |
| AST > 3xULN | 1 (<1%) | 0 |
| ALT > 2xULN | 1 (<1%) | 2 (1.6%) |
| ALT > 3xULN | 0 | 1 (<1%) |

*Mean follow-up approximately 52 weeks
**Mean follow-up approximately 43 weeks

The data reported in Tables XI–XIV evidences that a pharmaceutical combination of the present invention, e.g., sustained release nicotinic acid and an immediate release HMG-CoA reductase inhibitor, given concomitantly, once per day at night before bedtime, is effective in reducing serum lipid levels, and in particular total cholesterol, VLDL-cholesterol, LDL-cholesterol, triglycerides, apolipoprotein B and Lp(a) levels, and is effective in reducing the total cholesterol to HDL-cholesterol ratio and the LDL-cholesterol to HDL-cholesterol ratio. The data reported in Tables XI–XIV also evidences that a pharmaceutical combination of the present invention, e.g., sustained release nicotinic acid and an immediate release HMG-CoA reductase inhibitor, given concomitantly, once per day at night before bedtime, is effective in enhancing or increasing HDL-cholesterol levels. Also, it is believed that the data reported in Tables XI–XIV evidences that a pharmaceutical combination of the present invention, e.g., sustained release nicotinic acid and an immediate release HMG-CoA reductase inhibitor, given concomitantly, once per day at night before bedtime, is more effective in reducing LDL-cholesterol levels than when either sustained release nicotinic acid or an immediate release HMG-CoA reductase inhibitor are given in similar dosages once per day at night before going to bed, but alone. Still further, it is believed that the data reported in Tables XI–XIV evidences that a pharmaceutical combination of the present invention, e.g., sustained release nicotinic acid and an immediate release HMG-CoA reductase inhibitor, given concomitantly, once per day at night before bedtime, is more effective in increasing HDL-cholesterol levels than when an immediate release HMG-CoA reductase inhibitor is given by itself in a similar dosage once per day at night before going to bed.

The data reported in Tables XI–XIV also evidences that such concomitant therapy, e.g., sustained release nicotinic acid and an immediate release HMG-CoA reductase inhibitor, given once per day at night before bedtime can be administered and the benefits achieved without inducing hepatotoxicity, myopathy or rhabdomyolysis, or at least without inducing in an appreciable number of individuals hepatotoxicity, myopathy or rhabdomyolysis to such a level that would require discontinuation of such therapy. Moreover, the data reported in Table XII evidences that such concomitant therapy, e.g., sustained release nicotinic acid and an immediate release HMG-CoA reductase inhibitor, given once per day at night before bedtime can be administered and the benefits achieved without adversely effecting glucose metabolism or uric acid levels, or without adversely effecting in at least an appreciable number of individuals glucose metabolism or uric acid levels to such an extent that discontinuation of such therapy would be required.

Based upon the foregoing disclosure, it should now be apparent that the pharmaceutical combinations, formulations, compositions and methods and the use thereof described herein will carry out the objectives set forth hereinabove. It is, therefore, to be understood that any variations evident in the pharmaceutical combinations, formulations, compositions and methods fall within the scope of the claimed invention and, thus, the selection of specific component elements can be determined without departing from the spirit of the invention herein disclosed and described. For example, sustained release excipients, binders and processing aids according to the present invention are not necessarily limited to those exemplified hereinabove. Thus, the scope of the invention shall include all modifications and variations that may fall within the scope of the attached claims.

Having described my invention, I claim:

1. A method of reducing the capacity of extended release nicotinic acid to provoke a flushing reaction in an individual when extended release nicotinic acid is orally administered in an effective lipid-altering amount as a single dose once a day during the evening hours or before or at bedtime, comprising orally pretreating the individual with an effective flush inhibiting amount of a flush inhibiting agent for a sufficient period of time prior to initiating the administration of the extended release nicotinic acid in the individual to inhibit or reduce prostaglandin $PGD_2$ induced by the extended release nicotinic acid; and orally administering the nicotinic acid to the pretreated individual in an effective lipid-altering amount as a single dose once a day during the evening hours or before or at bedtime without causing treatment-limiting hepatotoxicity and elevations in glucose and/or uric acid levels, whereby the capacity of the extended release nicotinic acid to provoke a flushing reaction in the pretreated individual is reduced or prevented.

2. A method of claim 1, wherein said method includes the further step of orally administering to the pretreated individual an HMG-CoA reductase inhibitor in an effective lipid-altering amount without causing treatment-limiting myopathy and rhabdomyolysis.

3. A method of claim 2, wherein said HMG-CoA reductase inhibitor oral administartion is concomitantly with said extended release nicotinic acid oral administration.

4. A method of claim 2, wherein the HMG-CoA reductase inhibitor is an extended release form or in an immediate release form.

5. A method of claim 2, wherein said HMG-CoA reductase inhibitor is selected from the group consisting of atorvastatin, cerivastatin, flavastatin, lovastatin, pravastatin and simvastatin.

6. A method of claim 1, wherein the flush inhibiting agent is a nonsteroidal anti-inflammatory agent.

7. A method of claim 6, wherein the nonsteroidal anti-inflammatory agent is selected from the group consisting of indomethacin, sulindac, etodolac, aspirin, salicylate salts, ibuprofen, fluribprofen, fenoprophen, suprofen, benoxaprofen, ketoprofen, carprofen, naproxen, sodium naproxen, aclofenac, diclofenac, fenclofenac, tolmectin, zomepirac, meclofenamate, mefanamic acid, oxyphenbutazone, phenylbutazone and piroxicam.

8. A method of claim 1, wherein the flush inhibiting agent is aspirin.

9. A method of claim 8, wherein said oral administration of the aspirin comprises orally administering the aspirin in one to four doses per day during said pretreatment.

10. A method of claim 8 wherein said method includes the further step of orally administering the aspirin as the flush inhibiting agent in an amount of between about 80 mg and 1000 mg daily during said pretreatment.

11. A method of claim 2, wherein the flush inhibiting agent is aspirin.

12. A method of claim 11, wherein said oral administration of the aspirin comprises orally administering the aspirin in one to four doses per day during said pretreatment.

13. A method of claim 11, wherein said oral administration of the aspirin comprises orally administering the aspirin in one or two doses per day during said pretreatment.

14. A method of claim 11, wherein said method includes the further step of orally administering the aspirin as the flush inhibiting agent in an amount of between about 80 mg and about 1000 mg daily during said pretreatment.

15. A method of claim 11, wherein said method includes the further step of orally administering the aspirin as the flush inhibiting agent in an amount of between about 80 mg and about 650 mg daily during said pretreatment.

16. A method of claim 11, wherein said method includes the further step of orally administering the aspirin as the flush inhibiting agent in an amount of between about 80 mg and about 325 mg daily during said pretreatment.

17. A method of claim 11, wherein said method includes the further step of orally administering a nicotinic acid compound to the pretreated individual in an effective lipid-altering amount.

18. A method of claim 17, wherein the extended release nicotinic acid compound is selected from the group consisting of nicotinyl alcohol tartrate, d-glucitol hexanicotinate, aluminum nicotinate, niceritrol, d, 1-alpha-tocopheryl nicotinate, 6-OH-nicotinic acid, nicotinaria acid, nicotinamide, nicotinamide-N-oxide, 6-OH-nicotinamide, NAD, N-methyl-2-pyriidine-8-carboxamide, N-methylnicotinamide, N-ribosyl-2-pyridone-5-carboxide, N-methyl-4-pyridone-5-carboxamide, bradilian, sorbinicate, hexanicite, ronitol, and lower alcohol esters of nicotinic acid.

19. A method of claim 11, wherein said method includes the further step of orally administering a cholestyramine to the pretreated individual in an effective lipid-altering amount.

20. A method of claim 11, wherein said method includes the further step of orally administering a colestipol to the pretreated individual in an effective lipid-altering amount.

21. A method of (a) altering serum lipid levels in an individual without causing treatment-limiting hepatotoxicity, myopathy, rhabdomyolysis and elevations in glucose and/or uric acid levels in the individual and (b) reducing the capacity of an extended release nicotinic acid to provoke a flushing reaction in the individual when the extended release nicotinic acid is orally administered in an effective lipid-altering amount as a single dose once a day during the evening hours or before or at bedtime, comprising orally pretreating the individual with an effective flush inhibiting amount of a flush inhibiting agent for a sufficient period of time prior to initiating administration of the extended release nicotinic acid in the individual to inhibit or reduce prostaglandin $PGD_2$ induced by the extended release nicotinic acid, and orally administering an oral solid dosage form comprised of an effective lipid-altering amount of the extended release nicotinic acid and an effective lipid-altering amount of an immediate release HMG-CoA reductase inhibitor to the pretreated individual as a single dose once a day during the evening hours or before or at bedtime, whereby the capacity of the extended release nicotinic acid to provoke a flushing reaction in the pretreated individual is reduced or prevented and the serum lipid levels in the individual are altered.

22. A method of claim 21, wherein the oral solid dosage form is a tablet.

23. A method of claim 21, wherein the extended release nicotinic acid is coated with the immediate release HMG-CoA reductase inhibitor.

24. A method of claim 23, wherein the oral solid dosage form is a tablet.

25. A method of claim 22, wherein the tablet includes an inner core containing the extended release nicotinic acid and a coating layer containing the immediate release HMG-CoA reductase inhibitor, wherein the inner core is coated with the coating layer.

26. A method of claim 21, wherein the oral solid dosage form contains the extended release nicotinic acid in an amount between about 250 mg and about 1,000 mg and the immediate release HMG-CoA reductase inhibitor in an amount between about 0.05 mg and about 80 mg.

27. A method of claim 22, wherein the oral solid dosage form contains the extended release nicotinic acid in an amount between about 250 mg and about 1,000 mg and the immediate release HMG-CoA reductase inhibitor in an amount between about 0.05 mg and about 80 mg.

28. A method of claim 23, wherein the oral solid dosage form contains the extended release nicotinic acid in an amount between about 250 mg and about 1,000 mg and the immediate release HMG-CoA reductase inhibitor in an amount between about 0.05 mg and about 80 mg.

29. A method of claim 24, wherein the oral solid dosage form contains the extended release nicotinic acid in an amount between about 250 mg and about 1,000 mg and the immediate release HMG-CoA reductase inhibitor in an amount between about 0.05 mg and about 80 mg.

30. A method of claim 25, wherein the oral solid dosage form contains the extended release nicotinic acid in an amount between about 250 mg and about 1,000 mg and the immediate release HMG-CoA reductase inhibitor in an amount between about 0.05 mg and about 80 mg.

* * * * *